United States Patent [19]

Daniels et al.

[11] 4,053,591

[45] Oct. 11, 1977

[54] 5-DEOXY-4,6-DI-O-(AMINOGLYCOSYL)-1,3-DIAMINOCYCLITOLS, METHODS FOR THEIR MANUFACTURE, METHOD FOR THEIR USE AS ANTIBACTERIAL AGENTS AND COMPOSITIONS USEFUL THEREFOR

[75] Inventors: Peter J. L. Daniels, Cedar Grove; Stuart W. McCombie, East Orange, both of N.J.

[73] Assignee: Schering Corporation, Kenilworth, N.J.

[21] Appl. No.: 701,387

[22] Filed: June 30, 1976

[51] Int. Cl.$^2$ .................. A61K 31/71; C07H 15/22
[52] U.S. Cl. .................................... 424/180; 195/96; 195/31 R; 536/10; 536/17
[58] Field of Search .................. 536/17, 10; 424/180

[56] References Cited

U.S. PATENT DOCUMENTS

| | | | |
|---|---|---|---|
| 3,828,021 | 8/1974 | Beattie et al. | 536/17 |
| 3,868,360 | 2/1975 | Daniels et al. | 536/17 |
| 3,920,628 | 11/1975 | Daniels et al. | 536/17 |
| 3,972,930 | 8/1976 | Daum et al. | 260/563 R |
| 3,982,996 | 9/1976 | Daum et al. | 195/29 |
| 4,003,922 | 1/1977 | Kavadias et al. | 260/348.5 |

OTHER PUBLICATIONS

Perkins, "J. Chem. Soc.", No. 16, pp. 1574–1585, 1975.

*Primary Examiner*—Johnnie R. Brown
*Attorney, Agent, or Firm*—Mary S. King

[57] ABSTRACT

5-Deoxy-4,6-di-O-(aminoglycosyl)-1,3-diaminocyclitols, useful antibacterial agents, are prepared by the reaction of the corresponding 5-O-thioformyl-4,6-di-O-(aminoglycosyl)-1,3-diaminocyclitol having all amino functions and all primary and secondary hydroxyl groups protected, with an organotin hydride (preferably tri-n-butylstannane) in an inert aprotic solvent under an inert atmosphere at temperatures of at least about 100° C, followed by removal of said hydroxyl and amino protecting groups.

15 Claims, No Drawings

5-DEOXY-4,6-DI-O-(AMINOGLYCOSYL)-1,3-DIAMINOCYCLITOLS, METHODS FOR THEIR MANUFACTURE, METHOD FOR THEIR USE AS ANTIBACTERIAL AGENTS AND COMPOSITIONS USEFUL THEREFOR

FIELD OF INVENTION

This invention relates to novel compositions-of-matter, to methods for their manufacture, to pharmaceutical formulations and to methods for their use as antibacterial agents.

More specifically, this invention relates to novel 4,6-di-O-(aminoglycosyl)-2,5-dideoxystreptamines having anti-bacterial activity, to methods for their manufacture, to pharmaceutical compositions thereof and to methods for their use in treating bacterial infections.

In particular, this invention relates to 5-deoxy derivatives of 4,6-di-O-(aminoglycosyl)-2-deoxystreptamine anti-bacterial agents including the gentamicins, sisomicin, verdamicin, tobramycin, the kanamycins, Antibiotics G-418, 66-40B, 66-40D, JI-20A, JI-20B and G-52, and 1-N-acyl, 1-N-alkyl, 2'-N-alkyl, 6'-N-alkyl, 1,2'-di-N-alkyl and 1,6'-di-N-alkyl derivatives of the foregoing.

This invention also relates to a process for preparing the foregoing 4,6-di-O-(aminoglycosyl)-2,5-dideoxystreptamines, to pharmaceutical compositions comprising said 4,6-di-O-(aminoglycosyl)-2,5-dideoxystreptamines and to the method of using said pharmaceutical compositions to elicit an antibacterial response in a warm blooded animal having a susceptible bacterial infection.

PRIOR ART

Known in the art are broad spectrum antibacterial agents which may be classified chemically as 4,6-di-O-(aminoglycosyl)-1,3-diaminocyclitols. Valuable antibacterial agents of this group are those wherein the aminocyclitol is 2-deoxystreptamine. Particularly valuable antibacterials of the 4,6-di-O-(aminoglycosyl)-2-deoxystreptamines are those wherein the aminoglycosyl group at the 6-position is a garosaminyloxy radical. Within the class of 4-O-aminoglycosyl-6-O-garosaminyl-2-deoxystreptamines are antibiotics such as gentamicins B, $B_1$, $C_1$, $C_{1a}$, $C_2$, $C_{2a}$, $C_{2b}$ and $X_2$; sisomicin, verdamicin, Antibiotic G-418, Antibiotic G-52, Antibiotic JI-20A and Antibiotic JI-20B.

Also described in the art (South African Patent No. 74/4938, equivalent to co-pending U.S. Serial No. 476,638 filed June 5, 1974 now U.S. Pat. No. 4,011,390, of common assignee as the instant application) is an antibiotic known as Antibiotic Mu-2 (identified therein as mutamicin 2) which has the structural formula of 5-deoxysisomicin and which is prepared microbiologically by cultivating the organism Micromonospora inyoensis strain 1550F-1G (NRRL 3292) in an aqueous nutrient medium containing 2,5-dideoxystreptamine. Additionally, in South African Patent No. 74/4939 (and in copending application Ser. No. 492,998 filed July 30, 1974 now abandoned, of common assignee as the instant application) are described 1-N-alkyl derivatives of Antibiotic Mu-2 (i.e. 1-N-alkyl-5-deoxysisomicins) which are antibacterial agents prepared from Antibiotic Mu-2 by chemical transformations such as by reaction thereof with an aldehyde at about pH 5 followed by the in situ reduction of the Schiff's base thereby formed with a hydridedonor reducing agent. In South African Patent No. 74/4939 are also described 1-N-acyl-Antibiotic Mu-2 (i.e. 1-N-acyl-5-deoxysisomicins) useful mainly as intermediates since, upon reduction thereof, they are converted to the 1-N-alkyl-Antibiotic Mu-2 antibacterial agents.

By our invention, we have discovered a method whereby the hydroxyl function at the 5-position of the 2-deoxystreptamine or derivative thereof in a 4,6-di-O-(aminoglycosyl)-2-deoxystreptamine is removed to form heretofore unavailable 4,6-di-O-(aminoglycosyl)-2,5-dideoxystreptamines which are valuable broad spectrum antibacterial agents. Preferred compounds of my invention include 4,6-di-O-(aminoglycosyl)-2,5-dideoxystreptamines, particularly those wherein the 6-O-aminoglycosyl group is 6-O-garosaminyl, which derivatives exhibit an improved antibacterial spectrum over that of the parent compound.

GENERAL DESCRIPTION OF THE INVENTION COMPOSITION-OF-MATTER ASPECT

Included among the antibacterially active compositions-of-matter of this invention are 4,6-di-O-(aminoglycosyl)-2,5-dideoxystreptamines selected from the group consisting of 5-deoxygentamicin B, 5-deoxygentamicin $B_1$, 5-deoxygentamicin $C_1$, 5-deoxygentamicin $C_{1a}$, 5-deoxygentamicin $C_2$, 5-deoxygentamicin $C_{2a}$, 5-deoxygentamicin $C_{2b}$, 5-deoxygentamicin $X_1$, 5-deoxygentamicin $X_2$, 5-deoxyverdamicin, 5-deoxytobramycin, 5-deoxy-Antibiotic G-418, 5-deoxy-Antibiotic 66-40B, 5-deoxy-Antibiotic 66-40D, 5-deoxy-Antibiotic JI-20A, 5-deoxy-Antibiotic JI-20B, 5-deoxy-Antibiotic G-52, 5-deoxykanamycin A, 5-deoxykanamycin B, 5-deoxykanamycin C, 5,3',4'-trideoxykanamycin B, 5-deoxy-Aminoglycoside XK-88-5, and the 1-N-X derivatives thereof;

wherein X is a substituent selected from the group consisting of $-CH_2Z$ and

wherein Z is a member selected from the group consisting of hydrogen, alkyl, alkenyl, cycloalkyl, cycloalkylalkyl, hydroxyalkyl, aminoalkyl, alkylaminoalkyl, aminohydroxyalkyl, alkylaminohydroxyalkyl, phenyl, benzyl, and tolyl, said substituent Z having up to 7 carbon atoms, and, when substituted by amino and hydroxy, bearing the substituents on different carbon atoms;

the 2'-N-$CH_2Z$, 6'-N-$CH_2Z$, 1,2'-di-N-$CH_2Z$ and 1,6'-di-N-$CH_2Z$ derivatives thereof wherein Z is as hereinabove defined;

and the pharmaceutically acceptable acid addition salts thereof.

Included among the substituents contemplated for the moiety $CH_2Z$ in the novel compounds are straight and branched chain alkyl groups such as ethyl, n-propyl, n-butyl, β-methylpropyl, n-pentyl, β-methylbutyl, γ-methylbutyl and β,β-dimethylpropyl; n-hexyl, δ-methylpentyl, β-ethylbutyl, γ-ethylbutyl, n-heptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; alkenyl groups such as β-propenyl, β-methylpropenyl, β-butenyl, β-methyl-β-butenyl, β-ethyl-β-hexenyl; cyclic groups such as cyclopropylmethyl, cyclopentylmethyl, cyclohexylmethyl and cyclopentylethyl; aromatic groups such as o-, m-, p-methylbenzyl;

hydroxy substituted sraight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, ω-hydroxyoctyl; amino substituted straight and branched chain alkyl groups such as ε-aminopentyl, β-aminopropyl, γ-aminopropyl, δ-aminobutyl, β-amino-γ-methylbutyl and ω-aminooctyl and mono-N-alkylated derivatives thereof such as the N-methyl, N-ethyl and N-propyl derivatives, e.g. ε-methylaminopentyl, β-methylaminopropyl, β-ethylaminopropyl, δ-methylaminobutyl, β-methylamino-γ-methylbutyl and ω-methylaminobutyl; amino and hydrocy disubstituted straight and branched chain alkyl groups such as β-hydroxy-ε-aminopentyl, γ-hydroxy-γ-methyl-δ-aminobutyl, β-hydroxy-δ-aminobutyl, β-hydroxyγ-aminopropyl, and β-hydroxy-β-methyl-γ-aminopropyl; and mono-N-alkylated derivatives thereof such as β-hydroxyε-methylaminopentyl, γ-hydroxy-γ-methyl-δ-methylaminobutyl, β-hydroxy-δ-methylaminobutyl, β-hydroxy-γ-ethylaminopropyl and β-hydroxy-β-methyl-γ-methylaminopropyl.

Included among the substituents contemplated for the moiety

in the novel amide compounds are radicals similar to most of the radicals listed above for the moiety —CH₂Z but wherein the terminal methylene group is replaced by carbonyl, such as formyl, acetyl, propionyl, propenoyl, butyryl, isobutyryl, cyclopropylcarbonyl, benzoyl, hydroxyacetyl, aminoacetyl, 4-hydroxybutyryl, 4-aminobutyryl and the like.

Of the 1-N-CH₂Z, 2'-N-CH₂Z, 6'-N-CH₂Z, 1,2'-di-N-CH₂Z derivatives of this invention, preferred are those wherein the CH₂Z moiety has at least 2 carbon atoms, particularly those having 2 to 4 carbon atoms including compounds wherein —CH₂Z is ethyl, propyl, and δ-aminobutyl.

Of the 1-N-acyl derivatives of this invention, i.e.

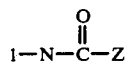

derivatives of the 4,6-di-O-(aminoglycosyl)-2,5-dideoxystreptamines of this invention, preferred are the lower alkanoyl derivatives having up to 4 carbon atoms, e.g. 1-N-acetyl, 1-N-propionyl and 1-N-butyryl derivatives which, upon reduction, are converted to the preferred 1-N-alkyl-5-deoxy derivatives of this invention. Other valuable 1-N-acyl derivatives are the 1-N-(3-amino-2-hydroxypropionyl), the 1-N-(4-amino-2-hydroxybutyryl) and the 1-N-(5-amino-2-hydroxyvaleryl)-4,6-di-O-(aminoglycosyl)-2,5-dideoxystreptamines.

Particularly useful antibacterial agents of my invention include 4,6-di-O-(aminoglycosyl)-2,5-dideoxystreptamines wherein the aminoglycoside radical at the 6-position is garosaminyloxy. Typical 4-O-aminoglycosyl-6-O-garosaminyl-2,5-dideoxystreptamines of this invention are 5-deoxygentamicin B, 5-deoxygentamicin B₁, 5-deoxygentamicin C₁, 5-deoxygentamicin C₁ₐ, 5-deoxygentamicin C₂, 5-deoxygentamicin C₂ₐ, 5-deoxygentamicin C₂ᵦ, 5-deoxygentamicin X₁, 5-deoxygentamicin X₂, 5-deoxyverdamicin, 5-deoxy-Antibiotic G-418, 5-deoxy-Antibiotic JI-20A, 5-deoxy-Antibiotic JI-20B, and 5-deoxy-Antibiotic G-52, and the 1-N-X, 2'-N-CH₂Z, 6'-N-CH₂Z, 1,2'-di-N-CH₂Z and 1,6'-di-N-CH₂Z derivatives thereof wherein X and Z are as hereinabove defined.

Other useful 4,6-di-O-(aminoglycosyl)-2,5-dideoxystreptamines of this invention include 5-deoxytobramycin, 5-deoxykanamycin A, 5-deoxykanamycin B, 5-deoxykanamycin C, 5,3',4'-trideoxykanamycin B, 5-deoxy-Antibiotics 66-40B and 66-40D, and 5deoxy-Aminoglycoside XK-88-5 and 1-N-X, 2'-N-CH₂Z, 6'-N-CH₂Z, 1,2'-di-N-CH₂Z and 1,6'-di-N-CH₂Z derivatives thereof wherein X and Z are as hereinabove defined.

The 4,6-di-O-(aminoglycosyl)-2,5-dideoxystreptamines of this invention are characterized by being white amorphous powders.

Also included within the composition-of-matter aspect of this invention are pharmaceutically acceptable acid addition salts of the 4,6-di-O-(aminoglycosyl)-2,5-dideoxystreptamines and derivatives thereof, which salts are made according to known procedures such as by neutralizing the free base with the appropriate acid, usually to about pH 5. Suitable acids for this purpose include acids such as hydrochloric, sulfuric, phosphoric, hydrobromic and the like. The physical embodiments of the acid addition salts of the 4,6-di-O-(aminoglycosyl)-2,5-dideoxystreptamines are characterized by being white solids which are soluble in water and insoluble in most polar and non-polar organic solvents.

The 4,6-di-O-(aminoglycosyl)-2,5-dideoxystreptamines, particularly those wherein the 6-O-aminoglycosyl is 6-O-garosaminyl, and their non-toxic, pharmaceutically acceptable, acid addition salts, in general, exhibit broad spectrum antibacterial activity and possess an improved antibacterial spectrum over that of the 5-hydroxy precursor. Thus, for example, 4-O-aminoglycosyl-6-O-garosaminyl-2,5-dideoxystreptamines and particularly 1-N-substituted derivatives thereof, are more active against organisms which inactivate the parent antibiotics by acetylation of the 3-amino group and/or by adenylylation of the 2''-hydroxyl group. Of these, some also exhibit anti-protozoal, anti-amoebic and anthelmintic properties.

Particularly valuable 4-O-aminoglycosyl-6-O-garosaminyl-2,5-dideoxystreptamines include the 5-deoxy derivatives of gentamicin C₁ₐ, gentamicin C₂, gentamicin C₂ₐ, verdamicin, as well as 5-deoxy-Antibiotic 66-40D and the 1-N-ethyl-, 1,2'-di-N-ethyl-, and 1,6'-di-N-ethyl derivatives thereof, which are broad spectrum antibacterial agents, being active against gram positive bacteria (e.g. *Staphylococcus aureus*) and gram negative bacteria (e.g. *Escherichia coli* and *Pseudomonas aeruginosa*) including bacteria resistant to the parent compounds as determined by standard dilution tests.

Also of particular value are the 1-N-(3-amino-2-hydroxypropionyl)-, 1-N-(4-amino-2-hydroxybutyryl)-, and the 1-N-(5-amino-2-hydroxyvaleryl)- derivatives of 5-deoxygentamicin B, 5-deoxygentamicin B₁, and 5-deoxykanamycin A. The acyl group at position 1 of the foregoing compounds may be in the racemic R,S-form or in the R-form or S-form. In this specification and in the claims, where a specific enantiomeric form is not specified in a compound name, all forms are implicitly included. Thus, the compound name 1-N-(β-amino-α-hydroxypropionyl)-5-deoxygentamicin B₁ includes 1-N-(R,S-β-amino-α-hydroxypropionyl)-5-deoxygentamicin B₁, 1-N-(R-β-amino-α-hydroxypropionyl)-5-deoxygentamicin B and 1-N-(S-β-amino-α-hydroxypropionyl)-5-deoxygentamicin B.

PROCESS ASPECT OF THE INVENTION

The process sought to be patented in its process aspect resides in the concept of a process for the preparation of a 5-deoxy-4,6-di-O-(aminoglycosyl)-1,3-diaminocyclitol which comprises the reaction of the corresponding 5-O-thioselenyl- or 5-O-thioformyl-4,6-di-O-(aminoglycosyl)-1,3-diaminocyclitol having all amino functions protected by an amino protecting group, Y, and all primary and secondary hydroxyl groups protected by a hydroxy protecting group, R; with at least a molar equivalent of an organotin hydride in an inert aprotic solvent at a temperature of at least about 100° C and under an inert atmosphere; followed by removal of said amino protecting groups, Y, and said hydroxyl protecting groups, R.

The organotin hydride reagents and their method of preparation are well known in the art. For use in our process, the organotin hydride reagent may contain any organic radical of any molecular weight, including alkyltin hydrides (e.g. trimethyltin hydride and triethyltin hydride), aryltin hydrides (e.g. triphenyltin hydride) and aralkyltin hydrides (e.g. tri-benzyltin hydride). A preferred reagent for use in our process is tri-n-butyltin hydride.

The temperature at which our process is carried out ought be at about 100° C in order that the intermediate formed upon reaction of an organotin hydride with the 5-O-thioformyl-(or 5-O-selenoformyl-) ester will fragment to form the desired deoxy compound. The upper limit of the temperature range at which our process is advantageously carried out is determined by the temperature at which the O-thioformyl ester will decompose.

Solvents useful in our process are preferably aprotic solvents which boil at least about 100° C, preferably in the range of 100° to 150° C. Toluene or xylene are usually employed. The solvent need not be anhydrous, but too much water ought not be present.

Our process is carried out in an inert atmosphere such as argon or nitrogen.

Useful intermediates of our process are the 5-O-selenoformyl- or the 5-O-thioformyl esters of the 4,6-di-O-(aminoglycosyl)-1,3-diaminocyclitol from which the 5-hydroxyl group is to be removed. Of these, the 5-O-thioformyl esters are the preferred intermediate since they are more stable than the 5-O-selenoformyl esters and they lead to greater yields of purer deoxygenated product than do the corresponding O-selenoformyl esters.

The O-formyl ester intermediates of our process are compounds defined by the following structural formula I $$\overset{X}{\underset{\|}{ROC-H}} \qquad (I)$$

wherein R is the radical of the 4,6-di-O-(aminoglycosyl)-1,3-diaminocyclitol bonded to the oxygen by the methine carbon at C-5, and X is selenium or sulfur.

The starting compounds of our process may be any 4,6-di-O-(aminoglycosyl)-1,3-diaminocyclitol having antibacterial activity and a hydroxyl function at the 5-position and wherein any amino groups present are protected, preferably by benzyloxycarbonyl, substituted benzyloxycarbonyl (including o, m, and p-methoxybenzyloxycarbonyl), alkoxycarbonyl (e.g. methoxycarbonyl, n-butoxycarbonyl, tert.-butoxycarbonyl, octyloxycarbonyl) groups. Methods whereby the foregoing amino protected derivatives are prepared from the free amine as well as methods of converting an N-protected derivative to a free amino compound are well known in the art.

The starting compounds are also preferably devoid of substituents which are reduced by organotin hydrides such as nitro, nitroso, chlorine, bromine and iodine unless one wishes to concomitantly remove a 5-O-hydroxyl group and reduce any other reducible function in the compound.

Tertiary hydroxyl groups and secondary hydroxyl groups other than the secondary hydroxyl group to be removed by our process need not be protected prior to reaction with an organotin hydride; however, other secondary hydroxyl functions in the 4,6-di-O-(aminoglycosyl)-1,3-diaminocyclitol starting compounds are preferably protected prior to preparation of the requisite thioester or selenoester intermediate since the 5-hydroxyl function is extremely hindered, therefore the yields of desired thioformyl esters or selenoformyl esters are greater when the other secondary less hindered hydroxyl functions are protected. Any primary hydroxyl functions present in the organic starting compounds in our process ought be protected prior to preparation of the requisite 5-O-thioformyl or 5-O-selenoformyl esters since primary alcohols form O-thioformyl esters and O-selenoformyl esters which, under the conditions of our process, will also deoxygenate, albeit in small yields. Useful O-protecting groups for any primary and other secondary hydroxyl groups in the organic starting compound of the process of this invention include hydrocarboncarbonyl (e.g. benzoyl, acetyl, propionyl); alkoxycarbonyl (e.g. methoxycarbonyl, ethoxycarbonyl); aralkoxycarbonyl (e.g. benzyloxycarbonyl); cyclic ketals and cyclic acetals of neighboring hydroxyl groups including O-alkylidenes (e.g. O-isopropylidene), O-cycloalkylidenes (e.g. O-cyclohexylidene) and O-aralkylidene (e.g. O-benzylidene) derivatives; carbonyl derivatives of neighboring hydroxyl and amino functions (which, in essence, are cyclic carbonates and carbamates, respectively) and hydrolyzable ethers of primary hydroxyl groups (e.g. triphenylmethyl ether). Processes for preparing the foregoing O-protected derivatives as well as processes whereby they are removed to regenerate the free hydroxyl groups are well known in the art.

The O-thioformyl esters of formula I are conveniently prepared via an "amido chloride" route shown below in Diagram A wherein R is as defined for formula I:

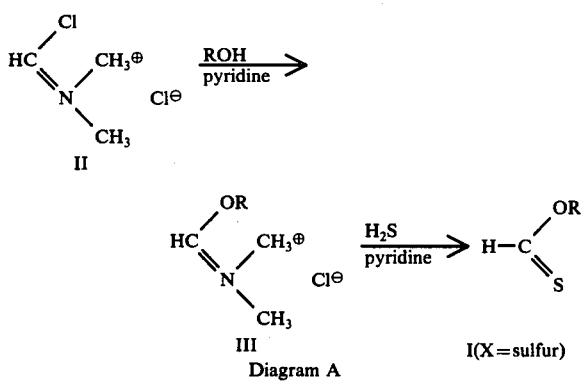

Diagram A

By this process, a "Vilsmeier salt" (II) is prepared by reaction of phosgene with an appropriate N,N'-dialkyl formamide, and condensed with the secondary alcohol at position 5 of the 4,6-di-O-(aminoglycosyl)-1,3-diaminocyclitol followed by treatment of the resulting imidinium chloride salt (III) with these and hydrogen sulfide. In this procedure, an excess of Vilsmeier salt is usually employed. Thus, when preparing an O-thioformate ester intermediate (i.e. a compound of formula I, e.g. 5-O-thioformylsisomicin), upon reaction of N,N-dimethylformamide and phosgene in dichloromethane at room temperature there is produced N,N-dimethyl-α-chloroformimidinium chloride (compound of formula II) which, upon reaction with a 4,6-di-O-(aminoglycosyl)-1,3-diaminocyclitol (e.g. 1,3,2',6'-tetra-N-ethoxycarbonyl-2''-O-benzoyl-3'',4''-N,O-carbonylsisomicin) followed by reaction of the imidinium chloride salt thereby produced (e.g. 1,3,2',6'-tetra-N-ethoxycarbonyl-2''-O-benzoyl-3'',4''-N,O-carbonylsisomicin-5-O-(N,N-dimethylformimidinium) chloride (a compound of formula III wherein R is the N,O-protected sisomicin radical) with hydrogen sulfide in pyridine whereby is produced an O-thioformylester of formula I (e.g. 1,3,2',6'-tetra-N-ethoxycarbonyl-5-O-thioformyl-2''-O-benzoyl-3'',4''-N,O-carbonylsisomicin) in good yields (e.g. 79% theory of the aforenamed N-protected-O-protected-5-O-thioformylsisomicin derivative).

O-selenoformylesters of formula I are prepared by the reaction of the secondary alcohol imidinium chloride intermediate (III) (prepared as described hereinabove as shown in Diagram A) with sodium hydroselenide, which is prepared by reaction of elemental selenium with sodium borohydride, i.e. as indicated below in Diagram B:

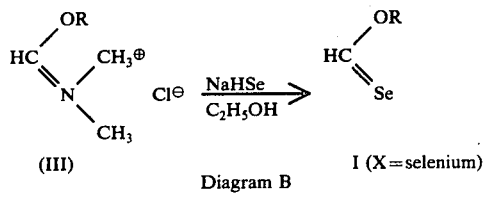

Diagram B

Usually, when preparing an O-selenoformate ester, sodium hydroselenide is made according to known procedures by reaction of selenium powder and sodium borohydride in ethanol. To the resulting reaction mixture at 0° C containing triethoxyborane in addition to sodium hydroselenide, there is added acetic acid and then the formimidinium chloride salt (III) intermediate (e.g. 1,3,2',6'-tetra-N-ethoxycarbonyl-2''-O-benzoyl-3'',4''-N,O-carbonylsisomicin-5-O-(N,N-dimethylformimidinium) chloride) and the reaction solution stirred at room temperature for about 30 minutes. The O-selenoformate ester (e.g. 1,3,2',6'-tetra-N-ethoxycarbonyl-5-O-selenoformyl-2''-O-benzoyl-3'',4''-N,O-carbonylsisomicin) thereby formed is then conveniently isolated and purified by utilizing conventional techniques such as extraction, recrystallization and chromatographic techniques.

By our invention, we have discovered that excellent yields of 5-O-thioformyl esters of 4,6-di-O-(aminoglycosyl)-1,3-diaminocyclitols are obtained by the above described method and that said 5-O-thioformyl esters are excellent intermediates for our deoxygenation process. The use of other 5-O-thioesters (or 5-O-selenoesters) in our deoxygenation process is an obvious equivalent of our claimed invention and is considered as within the scope thereof. We have found, however, that the preparation of thioesters (or selenoesters), other than O-thioformyl (or O-selenoformyl) esters is subject to steric hindrance and that, for example, the preparation of 5-O-thiobenzoates are sterically prohibited.

The per-N-protected-per-O-protected-5-O-thioformyl-(or selenoformyl)-4,6-di-O-(aminoglycosyl)-1,3-diaminocyclitol precursors for the corresponding 5-deoxy intermediates, are derived from known, unprotected-4,6-di-O-(aminoglycosyl)-1,3-diaminocyclitols including 4-O-aminoglycosyl-6-O-garosaminyl-2-deoxystreptamine antibiotics such as gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, Antibiotic G-418, Antibiotic JI-20A, Antibiotic JI-20B, and Antibiotic G-52; and 4,6-di-O-(aminoglycosyl)-2-deoxystreptamines such as gentamicin A, gentamicin X, tobramycin, Antibiotic 66-40B, Antibiotic 66-40D, kanamycins A, B, and C, 3', 4'-dideoxykanamycin B and aminoglycoside XK-88-5. Of the foregoing, preferred starting antibiotic precursors are gentamicins $C_1, C_{1a}, C_2, C_{2a}, C_{2b}$, Antibiotic 66-40D, verdamicin, Antibiotic G-52, and sisomicin, all of which are easily converted to preferred compounds of this invention, i.e. to the corresponding 5-deoxy-derivatives.

The aforementioned, 4,6-di-O-(aminoglycosyl)-1,3-diaminocyclitol antibiotics are known. Of the gentamicins, the starting compound referred to herein as gentamicin $X_2$ is also known in the art as gentamicin X. The starting compound referred to herein as gentamicin $C_{2a}$ is isolated and characterized as set forth in South African Patent 74/4939. The starting compound referred to herein as gentamicin $C_{2b}$, (described in J. Antibiotics Vol 28 No. 1, pp. 35-51 (1975)) is named in some prior art as gentamicin $C_{2a}$. The 1-N-substituted-4,6-di-O-(aminoglycosyl)-1,3-diaminocyclitol precursors including 1-N-alkyl and 1-N-acyl derivatives, unsubstituted or substituted by amino and/or hydroxyl functions, are described in South African Patent 74/4939. The 2'-N-alkyl and 1,2'-di-N-alkyl4,6-di-O-(aminoglycosyl)-1,3-diaminocyclitol precursors are prepared as described in copending U.S. application No. 628,637 filed Nov. 4, 1975, now abandoned, of common assignee as the instant application. Some 6'-N-alkyl-4,6-di-O-(aminoglycosyl)-1,3-diaminocyclitol precursors are prepared as described in copending U.S. application Ser. No. 666,715 filed Mar. 15, 1976, a continuation in part of U.S. Ser. No. 574,070 filed May 2, 1975, now abandoned of common assignee as the instant application. Others are known in the art.

Our process is the process of choice when preparing 5-deoxysisomicin (Antibiotic Mu-2) since greater yields of purer 5-deoxysisomicin are obtained by our process than by the prior art microbiological process. A preferred species of our process is that wherein sisomicin or 1-N-alkyl analogs thereof are converted to 5-deoxysisomicin (also known as Antibiotic Mu-2) or 1-N-$CH_2Z$-5-deoxysisomicins (e.g. the 1-N-ethyl-, 1-N-propyl-, and 1-N-δ-aminobutyl)-5-deoxysisomicins which are antibacterial agents, which advantageously are also active against adenylating and acetylating bacterial-strains resistant to sissomicin.

In general, when carrying out our process, a solution of a 5-O-selenoformyl ester or, preferably, a 5-O-thioformyl ester of a per-N-protected-4,6-di-O-(aminoglycosyl)-1,3-diaminocyclitol (e.g. 1,3,2',6'-tetra-N-benzyloxycarbonyl-5-O-thioformyl-2''-O-benzoyl-3'',4''-N,O-carbonyl-gentamicin $C_2$) toluene is added dropwise to a stirred solution of an organotin hydride (preferably tri-n-butylstannane) in toluene at reflux temperature, the quantity of said organotin hydride being at least equimolar to the quantity of aminoglycoside (usually 1.5 to 3 moles of trin-butylstannane is used per mole of the 5-O-thio (or seleno) ester). The reaction is continued until the intermediary ester is no longer present as determined by thin layer chromatography (usually 1 to 8 hours) then the 5-deoxy compound is isolated utilizing conventional techniques after removing any protecting groups which are present.

Usually, when carrying out our process, it is preferable to have all the functions desired in the final 5-deoxy derivative of this invention present in the 4,6-di-O-(aminoglycosyl)-1,3-diaminocyclitol precursor. Thus, for example, when preparing 1-N-ethyl-5-deoxyisomicin or 1-N-ethyl-5-deoxyverdamicin, the starting compounds of choice are the corresponding 1-N-ethyl-sisomicin and 1-N-ethylverdamicin. Alternatively, the 5-hydroxyl function can be removed from a 4,6-di-O-(aminoglycosyl)-1,3-diaminocyclitol by our process and substituents then introduced into the 5-deoxy derivative thereby produced by methods known in the art. This alternate procedure is the method of choice when preparing 1-N-alkyl and 1-N-acyl-5-deoxy-derivatives wherein the alkyl or acyl function is substituted by both amino and hydroxyl. Thus, for example, when preparing 1-N-(S-β-amino-δ-hydroxypropionyl)-5-deoxygentamicin B, a preferred method involves first converting gentamicin B to 5-deoxygentamicin B by reaction of 1,3,6'-tri-N-benzyloxycarbonyl-5-O-thioformyl-2',3',4',2''-tetra-O-benzoyl-3'',4''-N,O-carbonylgentamicin B with tri-n-butylstannane followed by removal of the amino and hydroxy protecting groups, and then converting the 5-deoxygentamicin B to 1-N-(S-β-amino-δ-hydroxypropionyl)-5-deoxygentamicin B utilizing techniques known in the art and as described in the Examples.

The processes described hereinabove are illustrated in detail hereinbelow in the Preparations and Examples which should not be construed as limiting the scope of my invention, obvious equivalents of which, apparent to one skilled in the art, being considered as included within the scope of this invention.

PREPARATION 1

TETRA-N-BENZYLOXYCARBONYL-5-O-THIOFORMYL-2''-O-BENZOYL-3'',4''-N,O-CARBONYLGENTAMICINS

A. 1,3,2',6',3''-Penta-N-Benzyloxycarbonylgentamicins 1. 1,3,2',6',3''-Penta-N-Benzyloxycarbonylgentamicin $C_2$ Stir vigorously in water (300 ml.) a mixture of gentamicin $C_2$ (30 gm.) and potassium carbonate (50 gm.) and add benzyl chloroformate (120 gm.) dropwise during a 2 hour period. Stir the reaction mixture overnight, separate the solid by filtration, wash with water then hexane. Dissolve the solid in chloroform (500 ml.), filter the solution over anhydrous sodium sulfate, concentrate to about 180 ml., then add the concentrated solution dropwise to a well-stirred mixture of ether (500 ml.) and hexane (2.5 liters). Separate the resultant precipitate by filtration, wash with hexane and dry at 60° C in vacuo to give 1,3,2',6',3''-penta-N-benzylgentamicin $C_2$; yield 67.5 gm. (91% theory); m.p. 100°-102° C; $[\alpha]_D^{26} + 76.4°$ (chloroform, c=0.38).

2. In the procedure of Preparation 1A(1), instead of gentamicin $C_2$ utilize as starting compounds each of gentamicin $C_1$, $C_{1a}$, $C_{2a}$ and $C_{2b}$ to obtain, respectively, 1,3,2',6',3''-penta-N-benzyloxycarbonylgentamicin $C_1$, 1,3,2',6',3''-penta-N-benzyloxycarbonylgentamicin $C_{1a}$, 1,3,2',6',3''-penta-N-benzyloxycarbonylgentamicin $C_{2a}$, and 1,3,2',6',3''-penta-N-benzyloxycarbonylgentamicin $C_{2b}$.

B. 1,3,2',6'-Tetra-N-Benzyloxycarbonyl-3'',4''-N,O-Carbonylgentamicins 1. 1,3,2',6'-Tetra-N-Benzyloxycarbonyl-3'',4''-N,O-Carbonylgentamicin $C_2$ To a solution of 1,3,2',6',3''-penta-N-benzyloxycarbonylgentamicin $C_2$ (30 gm.) in dry dimethylformamide (120 ml.) add hexane-washed sodium hydride (from 3 gm. of 50% dispersion). Stir the mixture at room temperature for 4 hours under an atmosphere of dry nitrogen. Add acetic acid (10 ml.) followed by methanol (20 ml.). Evaporate the mixture to a small volume, add 200 ml. of chloroform to the resultant residue, wash the chloroform solution with 5% aqueous sodium bicarbonate (100 ml.), dry over sodium sulfate and concentrate to a volume of about 60 ml. Add the concentrated solution dropwise to a well-stirred mixture of ether (200 ml.) and hexane (800 ml.). Separate the resultant solid by filtration and dry at 60° C in vacuo to give 1,3,2',6'-tetra-N-benzyloxycarbonyl-3'',4''-N,O-carbonylgentamicin $C_2$; yield 25.5 gm. (93% theory); m.p. 93°-96° C; $[\alpha]_D^{26} + 66.2°$ (chloroform, c=0.43).

2. In the procedure of Preparation 1B(1), utilize as starting compounds the penta-N-benzyloxycarbonyl derivatives prepared in Preparation 1A(2) to obtain, respectively, 1,3,2',6'-tetra-N-benzyloxycarbonyl-3'',4''-N-O-carbonylgentamicin $C_1$, 1,3,2',6'-tetra-N-benzyloxycarbonyl-3'',4''-N,O-carbonylgentamicin $C_{1a}$, 1,3,2',6'-tetra-N-benzyloxycarbonyl-3'',4''-N,O-carbonylgentamicin $C_{2a}$, 1,3,2',6'-tetra-N-benzyloxycarbonyl-3'',4''-N,O-carbonylgentamicin $C_{2b}$.

C. 1,3,2',6'-Tetra-N-Benzyloxycarbonyl-2''-O-Benzoyl-3'',4''-N,O-Carbonylgentamicins 1. 1,3,2',6'-Tetra-N-Benzyloxycarbonyl-2''-O-Benzoyl-3'',4''-N,O-Carbonylgentamicin $C_2$ To a solution of 1,3,2',6'-tetra-N-benzyloxycarbonyl-3'',4''-N,O-carbonylgentamicin $C_2$ (20 gms.) in dry pyridine (250 ml.) add benzoyl chloride (7.5 gms.) and stir at room temperature for three hours. Add methanol (10 ml.), then evaporate the solution in vacuo, dissolve the resultant residue in chloroform, wash the chloroform solution with dilute sulfuric acid and then water, dry the chloroform solution over sodium sulfate and evaporate. Dissolve the resultant residue in methylene chloride (80 ml.) and add the solution dropwise to a stirred solution of hexane (600 ml.) and ethyl acetate (200 ml.). Separate the resultant precipitate by filtration, wash the precipitate with hexane and dry at 60° C at 1 millimeter pressure to obtain 1,3,2',6'-tetra-N-benzyloxycarbonyl-2''-O-benzoyl-3'',4''-N,O-carbonylgentamicin $C_2$, yield 21.4 gms., (97% theory); m.p. 101°-105° C; $[\alpha]_D^{26} + 75.2°$ (chloroform, c=0.42).

2. In the procedure of above Preparation 1C(1), utilize as starting compounds each of the tetra-N-benzyloxycarbonyl-3'',4''-N,O-carbonylgentamicin derivatives prepared in Preparation 1B(2) to obtain, respectively, 1,3,2',6'-tetra-N-benzyloxycarbonyl-2''-O-benzoyl-3'',4''-N,O-carbonylgentamicin $C_1$, 1,3,2',6'-tetra-N- benzyloxycarbonyl-2''-O-benzoyl-3'',4''-N,O-carbonylgentamicin $C_{1a}$, 1,3,2',6'-tetra-N-benzyloxycarbonyl-2''-O-benzoyl-3'',4''-N,O-carbonylgentamicin $C_{2a}$, 1,3,2',6'-tetra-N-benzyloxycarbonyl-2''-O-benzoyl-3'',4''-N,O-carbonylgentamicin $C_{2b}$.

D. 1,3,2',6'-Tetra-N-Benzyloxycarbonyl-5-O-Thioformyl-2''-O-Benzoyl-3'',4''-N,O-Carbonylgentamicins 1. 1,3,2',6'-Tetra-N-Benzyloxycarbonyl-5-O-Thioformyl-2''-O-Benzoyl-3'',4''-N,O-Carbonylgentamicin $C_2$ Add N,N-dimethylformamide (1.5 ml.) to a stirred solution of phosgene in benzene (12.5%, 30 ml.), stir for 30 minutes, then evaporate the solvent under mositure-free conditions. To the resultant residue add with stirring dry methylene chloride (40 ml.) with ice cooling, then add a solution of 1,3,2',6'-tetra-N-benzyloxycarbonyl-2''-O-benzoyl-3'',4''-N,O-carbonylgentamicin $C_2$ (6.0 gms.) in methylene chloride (50 ml.) and pyridine (6 ml.). Stir for 5 minutes, add ethanol (2 ml.), then bubble dry hydrogen sulfide through the solution for 5 minutes. Allow the reaction mixture to stand at room temperature for 15 minutes, then add additional methylene chloride (100 ml.) to the reaction mixture and wash the solution twice with 200 ml. portions of 1 N hydrochloric acid, then wash with water and finally with sodium bicarbonate solution. Dry the methylene chloride solution over sodium sulfate and evaporate in vacuo. Dissolve the resultant residue in methylene chloride (30 ml.) and add the solution dropwise to a stirred mixture of ether (50 ml.) and hexane (500 ml.). Separate the resultant precipitate by filtration, wash with hexane, and dry at 60° C at 1 millimeter pressure to obtain 1,3,2',6'-tetra-N-benzyloxycarbonyl-5-O-thioformyl-2''-O-benzoyl-3'',4''-N,O-carbonylgentamicin $C_2$; yield 5.97 gms. (94% theory); m.p. 113°–116° C; $[\alpha]_D^{26}$ + 94.5° ; (chloroform, c=0.42).

2. In the procedure of Preparation 1D(1), utilize as starting compounds each of the tetra-N-benzyloxycarbonyl-2''-O-benzoyl-3'',4''-N,O-carbonyl derivatives prepared in Preparation 1C(2) to obtain, respectively, 1,3,2',6'-tetra-N-benzyloxycarbonyl-5-O-thioformyl-2''-O-benzoyl-3'',4''-N,O-carbonylgentamicin $C_1$, 1,3,2',6'-tetra-N-benzyloxycarbonyl-5-O-thioformyl-2''-O-benzoyl-3'',4''-N,O-carbonylgentamicin $C_{1a}$, 1,3,2',6'-tetra-N-benzyloxycarbonyl-5-O-thioformyl-2''-O-benzoyl-3'',4''-N,O-carbonylgentamicin $C_{2a}$, 1,3,2',6'-tetra-N-benzyloxycarbonyl-5-O-thioformyl-2''-O-benzoyl-3'',4''-N,O-carbonylgentamicin $C_{2b}$.

PREPARATION 2

TETRA-N-ETHOXYCARBONYL-5-O-THIOFORMYL-2''-O-BENZOYL-3'',4''-N,O-CARBONYLAMINOGLYCOSIDES

A. 1,3,2',6',3''-Penta-N-Ethoxycarbonylaminoglycosides 1. 1,3,2',6',3''-Penta-N-Ethoxycarbonylsisomicin To a solution of sisomicin (15.0 gms.) in methanol (500 ml.) add calcium hydroxide powder (35 gms.) and then ethyl chloroformate (17 ml.). Stir for 30 minutes, then add an additional portion of ethyl chloroformate (5 ml.) and continue stirring for one hour at room temperature. Filter the reaction mixture, wash the residue with methanol, then evaporate the combined filtrate and washings in vacuo to a volume of about 100 ml. Add chloroform (500 ml.) to the reaction mixture and wash the chloroform solution with water (250 ml.) containing acetic acid (10 ml.), then wash with a sodium bicarbonate solution (5%, 200 ml.). Dry the chloroform solution over sodium sulfate, filter, then evaporate in vacuo. Dissolve the resultant residue in dichloromethane (100 ml.) and add the solution dropwise to a mixture of ether (200 ml.) and hexane (1200 ml.) with vigorous stirring. Separate the resultant precipitate by filtration and dry at 60° C at 1 millimeter pressure to obtain 1,3,2',6',3''-penta-N-ethoxycarbonylsisomicin (yield 19.2 gms.) which can be used without further purification in the procedure of Preparation 2B(1).

2. In the procedure of Preparation 2A(1), in place of sisomicin utilize as starting compounds each of Antibiotic G-52, Antibiotic 66-40B, Antibiotic 66-40D and verdamicin to obtain, respectively, 1,3,2',6',3''-penta-N-ethoxycarbonyl-Antibiotic G-52, 1,3,2',6',3''-penta-N-ethoxycarbonyl-Antibiotic 66-40B, 1,3,2',6',3''-penta-N-ethoxycarbonyl-Antibiotic 66-40D, and 1,3,2',6',3''-penta-N-ethoxycarbonylverdamicin. B. 1,3,2',6'-Tetra-N-Ethoxycarbonyl-3'',4''-N,O-Carbonylaminoglycosides 1. 1,3,2',6'-Tetra-N-Ethoxycarbonyl-3'',4''-N,O-Carbonylsisomicin Stir under an atmosphere of nitrogen 1,3,2',6',3''-penta-N-ethoxycarbonylsisomicin (17.0 gms.) prepared as described in Preparation 2A(1) in dry dimethylformamide (80 ml.) and add a suspension of hexane-washed sodium hydride (from 2.1 gms. of 50% dispersion) in dimethylformamide (20 ml.). Stir for 30 minutes at room temperature, then add acetic acid (2.8 ml.) and methanol (5 ml.). Adjust the pH of the reaction mixture to about 6 by adding small quantities of acetic acid, then evaporate the reaction mixture at 40° C at 1 millimeter pressure. Dissolve the resultant residue in ethyl acetate (500 ml.), then wash the ethyl acetate solution with 20% aqueous sodium chloride (200 ml.), then dry over sodium sulfate and evaporate in vacuo, then dry the resultant foamy residue at 1 millimeter pressure for several hours to obtain 1,3,2',6'-tetra-N-ethoxycarbonyl-3'',4''-N,O-carbonylsisomicin, which is used without further purification in the procedure of Preparation 2C(1). 2. In the procedure of Preparation 2B(1) in place of penta-N-ethoxycarbonylsisomicin, utilize as starting compounds each of the penta-N-ethoxycarbonyl derivatives prepared in Preparation 2A(2) to obtain the corresponding 3'',4''-N,O-carbonyl derivatives thereof.

C. 1,3,2',6'-Tetra-N-Ethoxycarbonyl-2''-O-Benzoyl-3'', 4''-N,O-Carbonylaminoglycosides 1. 1,3,2',6'-Tetra-N-Ethoxycarbonyl-2''-O-Benzoyl-3'',4''-N,O-Carbonylsisomicin Dissolve the 1,3,2',6'-tetra-N-ethoxycarbonyl-3'', 4''-N,O-carbonylsisomicin prepared in Preparation 2B(1) in dry pyridine (150 ml.). Cool the solution in an ice bath, then add benzoyl chloride (4 ml.) and stir at room temperature for 3 hours. Dilute the reaction mixture with ethanol (10 ml.), evaporate in vacuo, dissolve the resultant residue in chloroform, then wash the chloroform solution with dilute sulfuric acid followed by sodium bicarbonate solution. Dry the solution over sodium sulfate, filter and evaporate. Chromatograph the resultant residue on alumina (Grade II, neutral, 700 gms.) eluting with 1% methanol:chloroform. Combine the eluates containing the desired product as determined by thin layer chromatography, then evaporate the combined fractions in vacuo to a residue comprising 1,3,2',6'-tetra-N-ethoxycarbonyl-2''-O-benzoyl-3'', 4''-N,O-carbonylsisomicin; yield 14.5 gms.; m.p. 131°–135° C; $[\alpha]_D^{26}$ + 99.8° (chloroform, c=0.62).

2. In the procedure of Preparation 2C(1), in place of tetra-N-ethoxycarbonyl-3'',4''-N,O-carbonylsisomicin, utilize as starting compounds each of the derivates prepared in above Preparation 2B(1) to obtain the corresponding 2"-O-benzoyl derivatives thereof.

D. 1,3,2',6'-Tetra-N-Ethoxycarbonyl-5-O-Thioformyl-2"-O-Benzoyl-3",4"-N,O-Carbonylaminoglycosides 1. 1,3,2',6'-Tetra-N-Ethoxycarbonyl-5-O-Thioformyl-2"-O-Benzoyl-3",4"-N,O-Carbonylsisomicin To a stirred solution of phosgen (ca 4 gms.) in benzene (30 ml.) add dimethylformamide (3 gms.). Stir the resultant suspension for 30 minutes, then evaporate, add dichloromethane (30 ml.) to the resultant residue and cool in an ice bath. To the cooled solution add 1,3,2',6'-tetra-N-ethoxycarbonyl-2"-O-benzoyl-3",4"-N,O-carbonylsisomicin (6.9 gms.) in dichloromethane (70 ml.) and pyridine (7 ml.). Stir the reaction mixture in an ice bath for 15 minutes, then bubble dry hydrogen sulfide gas through the reaction mixture for 5 minutes. Wash the solution with water, then dilute sulfuric acid and finally with sodium bicarbonate. Dry the solution over sodium sulfate, filter and evaporate. Dissolve the resultant residue in methylene chloride and pour onto a silica gel column (100 gms.). Elute first with chloroform, then elute with 2% methanol in chloroform combining like eluates containing the desired compound as determined by thin layer chromatography, evaporate the combined eluates in vacuo, dissolve the resultant residue in chloroform (30 ml.) and add the chloroform solution to hexane (500 ml.) with vigorous stirring. Separate the resultant precipitate by filtration, then dry the precipitate at 60° C at 1 millimeter pressure to obtain 1,3,2',6'-tetra-N-ethoxycarbponyl-5-O-thioformyl-2"-O-benzoyl-3",4"-N,O-carbonylsisomicin as a cream powder (yield 5.8 grams., 79%; m.p. 126°-130° C; $[\alpha]_D^{26}$ + 100.1° (chloroform, c=0.38).

2. In the procedure of Preparation 2D(1) instead of tetra-N-ethoxycarbonyl-2"-O-benzoyl-3",4"-N,O-carbonylsisomicin, utilize as starting compounds each of 1,3,2',6'-tetra-N-ethoxycarbonyl-2"-O-benzoyl-3",4"-N,O-carbonyl-Antibiotic G-52, 1,3,2',6'-tetra-N-ethoxycarbonyl-2"-O-benzoyl-3",4"-N,O-carbonyl-Antibiotic 66-40B, 1,3,2',6'-tetra-N-ethoxycarbonyl-2"-benzoyl-3",4"-N,O-carbonyl-Antibiotic 66-40D, and 1,3,2',6'-tetra-N-ethoxycarbonyl-2"-O-benzoyl-3",4"-N,O-carbonylverdamicin, to obtain the corresponding 5-O-thioformyl derivatives thereof.

PREPARATION 3

TETRA-N-BENZYLOXYCARBONYL-5-O-THIOFORMYL-2"-O-BENZOYL-3",4"-N,O-CARBONYL-1-N-ALKYLAMINOGLYCOSIDES

A. 1,3,2',6',3"-Penta-N-Benzyloxycarbonyl-1-N-Ethylaminoglycosides 1. 1,3,2',6',3"-Penta-N-Benzyloxycarbonyl-1-N-Ethylsisomicin To a stirred mixture of 1-N-ethylsisomicin (10.0 gms.), powdered calcium hydroxide (25 gms.) and methanol (250 ml.) cool to 0° C, add benzyl chloroformate (30 ml.). Stir at room temperature for one hour, then filter the reaction mixture, wash the residue with methanol, then concentrate the combined filtrate and methanol washings in vacuo to a volume of about 100 ml. Add chloroform (500 ml.) to the concentrate, wash the chloroform solution with 0.5 N hydrochloric acid and water, dry over potassium carbonate, filter and evaporate in vacuo. Dissolve the resultant residue in chloroform (60 ml.) and add the chloroform solution dropwise to a well stirred mixture of hexane (600 ml.) and ether (400 ml.). Separate the resultant precipitate by filtration, wash with hexane/ether and dry at 60° C at 1 millimeter pressure to obtain 1,3,2',6',3"-penta-N-benzyloxycarbonyl-1-N-ethylsisomicin, yield 21.2 gms. (83% theory), which may be used without further purification in the process of Preparation 3B(1). This compound may be purified further by chromatography on a silica gel column eluting with 1% methanol in chloroform to obtain 1,3,2',6',3"-penta-N-benzyloxycarbonyl-1-N-ethylsisomicin; m.p. 99°-103° C; $[\alpha]_D^{26}$ + 90.7° (chloroform, c=0.47).

2. In the procedure of Preparation 1A, in place of sisomicin utilize as starting compounds each of 1-N-ethyl-Antibiotic G-52, 1-N-ethyl-Antibiotic 66-40B, 1-N-ethyl-Antibiotic 66-40D and 1-N-ethylverdamicin to obtain the corresponding 1,3,2',6',3"-penta-N-benzyloxycarbonyl derivatives thereof. (3) In a manner similar to that described in Preparations 3A(1) and (2), treat each of the following 1-N-alkylaminoglycosides with powdered calcium hydroxide in methanol followed by benzyl chloroformate.

1-N-(n-propyl)sisomicin,
1-N-(δ-aminobutyl)sisomicin,
1-N-(n-propyl)-Antibiotic G-52,
1-N-(δ-aminobutyl)-Antibiotic G-52,
1-N-(n-propyl)-Antibiotic 66-40B,
1-N-(δ-aminobutyl)-Antibiotic 66-40B,
1-N-(n-propyl)-Antibiotic 66-40D,
1-N-(δ-aminobutyl)-Antibiotic 66-40D,
1-N-(n-propyl)verdamicin,
1-N-(δ-aminobutyl)verdamicin.

Isolate and purify each of the resultant products in a manner similar to that described to obtain the corresponding 1,3,2',6',3"-penta-N-benzyloxycarbonyl derivatives thereof.

B. 1,3,2',6'-Tetra-N-Benzyloxycarbonyl-3",4"-N,O-Carbonyl-1-N-Alkylaminoglycosides 1. 1,3,2',6'-Tetra-N-Benzyloxycarbonyl-3",4"-N,O-Carbonyl-1-N-Ethylsisomicin To a stirred solution of 1,3,2',6',3"-penta-N-benzyloxy carbonyl-1-N-ethylsisomicin (20 gms.) in dry dimethylformamide (100 ml.) add hexane-washed sodium hydride dispersion (50%, 2.0 gms.). Stir at room temperature for 45 minutes, then add acetic acid (5 ml.) in methanol (10 ml.) and remove the solvents at 50° C at one millimeter pressure. Dissolve the resultant residue in chloroform, wash the chloroform solution with 1 N ammonium hydroxide, dry over potassium carbonate and evaporate. Further purify by dissolving the resultant residue in chloroform (50 ml.), add the chloroform solution to a stirred hexane (900 ml.) and ether (300 ml.) mixture, filter the resultant precipitate, wash the resultant precipitate with hexane/ether and dry at 60° C at 1 millimeter pressure to obtain 1,3,2',6'-tetra-N-benzyloxycarbonyl-3",4"-N,O-carbonyl-1-N-ethylsisomicin.

2. In the procedure of Preparation 3B(1) utilize as starting compounds the penta-N-benzyloxycarbonyl derivatives prepared in Preparation 3A(2) to obtain the corresponding 3",4"-N,O-carbonyl derivatives thereof.

3. Similarly, carry out the procedure described in Preparation 3B(1) on the penta-N-benzyloxycarbonyl-1-N-alkylaminoglycoside derivatives prepared in Preparation 3A(3) to obtain the corresponding 1,3,2',6'-tetra-N-benzyloxycarbonyl-3",4"-N,O-carbonyl derivatives thereof.

C. 1,3,2',6'-Tetra-N-Benzyloxycarbonyl-2"-O-Benzoyl-3",4"-N,O-Carbonyl-1-N-Alkylaminoglycosides 1. 1,3,2',6'-Tetra-N-Benzyloxycarbonyl-2''-O-Benzoyl-3'',4''-N,O-Carbonyl-1-N-Ethylsisomicin Dissolve the 1,3,2',6'-tetra-N-benzyloxycarbonyl-3'',4''-N,O-carbonyl-1-N-ethylsisomicin prepared in Preparation 3B(1) in pyridine (90 ml.), add benzoyl chloride (4 ml.) and stir at room temperature for 4 hours. Add ethanol (10 ml.) and evaporate the solution in vacuo. Dissolve the resultant residue in chloroform, wash twice with dilute ammonium hydroxide, dry over potassium carbonate and evaporate in vacuo. Purify the resultant residue by chromatographing on silica gel (800 gms.) containing a small amount of solid sodium carbonate, eluting with 0.5% methanol: chloroform,. Combine the like fractions containing the desired product as determined by thin layer chromatography and evaporate the combined fractions in vacuo, then dry the resultant residue at 60° C at 1 millimter pressure to obtain 1,3,2',6'-tetra-N-benzyloxycarbonyl-2''-O-benzoyl-3'',4''-N,O-carbonyl-1-N-ethylsisomicin; yield 15.2 gms. (76% theory); m.p. 86°–90° C; $[\alpha]_D^{26}$ + 80.7° (chloroform, c=0.56). 2. In the procedure of Preparation 3C(1) utilize as starting compounds the tetra-N-benzyloxycarbonyl-3'',4''-N,O-carbonyl derivatives prepared in Preparation 3B(2) to obtain the corresponding 2''-O-benzoyl derivatives thereof. 3. In similar manner carry out the procedure of Preparation 3C(1) on the tetra-N-benzyloxycarbonyl-3'',4''-N,O-carbonyl-1-N-alkylaminoglycoside derivatives prepared in Preparation 3B(3) to obtain the corresponding 2''-O-benzoyl derivatives thereof.

D. 1,3,2',6'-Tetra-N-Benzyloxycarbonyl-5-O-Thioformyl-2''-O-Benzoyl-3'',4''-N,O-Carbonyl-1-N-Alkylaminoglycosides 1. 1,3,2',6'-Tetra-N-Benzyloxycarbonyl-5-O-Thioformyl-2''-O-Benzoyl-3'',4''-N,O-Carbonyl-1-N-Ethylsisomicin Add dimethylformamide (2.5 gms.) to phosgene (5 gms.) in benzene (40 ml.), stir for 30 minutes, then evaporate in vacuo the resultant residue in dry methylene chloride (30 ml.) and cool to 0° C. To the solution add with stirring a solution of 1,3,2',6'-tetra-N-benzyloxycarbonyl-2''-O-benzoyl-3'',4''-N,O-carbonyl-1-N-ethylsisomicin (7.0 gms.) in dry pyridine (10 ml.) and methylene chloride (40 ml.). Continue stirring the reaction mixture at 0° C for 15 minutes, then bubble hydrogen sulfide through the solution for 5 minutes, add pyridine (10 ml.) and allow the solution to stand at room temperature for 30 minutes. Dilute the reaction mixture with chloroform (100 ml.), then wash the solution with water (100 ml.), 0.2 N hydrochloric acid (twice with 100 ml. portions) and then with aqueous sodium bicarbonate. Dry over sodium sulfate, evaporate, dissolve the resultant residue in methylene chloride (40 ml.) and add this solution to a stirred mixture of hexane (400 ml.) and ether (100 ml.). Separate the resultant precipitate by filtration, wash the precipitate with hexane/ether and dry at 60° C at 1 millimeter pressure to give 1,3,2',6'-tetra-N-benzyloxycarbonyl-5-O-thioformyl-2''-O-benzoyl-3'',4''-N,O-carbonyl-1-N-ethylsisomicin; yield 6.70 gms. (95% theory).

2. In the procedure of Preparation 3D(1) utilize as starting compound each of tetra-N-benzyloxycarbonyl-2''-O-benzoyl-3'',4''-N,O-carbonyl derivatives prepared in Preparation 3C(2) to obtain the corresponding 5-O-thioformyl derivatives thereof. 3. Similarly, in the procedure of Preparation 3D(1) utilize as starting compounds each of the 1,3,2',6'-tetra-N-benzyloxycarbonyl-2''-benzoyl-3'',4''-N,O-carbonyl-1-N-alkylaminoglycosides prepared in Preparation 3C(3) to obtain the corresponding 5-O-thioformyl derivatives thereof.

PREPARATION 4

PER-N-BENZYLOXYCARBONYL-5-O-THIOFORMYL-POLY-O-BENZOYL AMINOGLYCOSIDES

A. Per-N-Benzyloxycarbonyl Aminoglycosides

In a manner similar to that described in Preparation 1A(1) treat each of the following aminoglycosides with an excess of benzyl chloroformate and potassium carbonate in aqueous methanol at room temperature:

gentamicin A, gentamicin $X_1$,
kanamycin A, kanamycin B,
kanamycin C, 3',4'-dideoxykanamycin B, and
Aminoglycoside XK-88-5.

Isolate and purify each of the resultant products in a manner similar to that described to obtain, respectively, 1,3,2',3''-tetra-N-benzyloxycarbonylgentamicin A,
1,3,2',3''-tetra-N-benzyloxycarbonylgentamicin $X_1$,
1,3,6',3''-tetra-N-benzyloxycarbonylkanamycin A,
1,3,2',6',3''-penta-N-benzyloxycarbonylkanamycin B,
1,3,2',3''-tetra-N-benzyloxycarbonylkanamycin C,
1,3,2',6',3''-penta-N-benzyloxycarbonyl-3',4'-dideoxykanamycin B,
1,3,2',6',2'',3''-hexa-N-benzyloxycarbonyl-Aminoglycoside XK-88-5.

B. Per-N-Benzyloxycarbonyl-Poly-O-Benzoyl Aminoglycosides

In a manner similar to that described in Preparation 1C(1) treat each of the per-N-benzyloxycarbonyl aminoglycosides prepared in Preparation 4A in pyridine with benzoyl chloride, the quantity of which is in excess of the molar quantity of aminoglycoside times the number of hydroxyl functions present therein. Isolate and purify each of the resultant products in a manner similar to that described in Preparation 1C(1) to obtain, respectively, 1,3,2',3''-tetra-N-benzyloxycarbonyl-3',4',6',2'',4''-penta-O-benzoylgentamicin A,
1,3,2',3''-tetra-N-benzyloxycarbonyl-3',4',6',2'',4''-penta-O-benzoylgentamicin $X_1$,
1,3,6',3''-tetra-N-benzyloxycarbonyl-2',3',4',2'',4'',6''-hexa-O-benzoylkanamycin A,
1,3,2',6',3''-penta-N-benzyloxycarbonyl-3',4',2'',4'',6''-penta-O-benzoylkanamycin B,
1,3,2',3''-tetra-N-benzyloxycarbonyl-3',4',6',2'',4'',6''-hexa-O-benzoylkanamycin C,
1,3,2',6',3''-penta-N-benzyloxycarbonyl-2'',4'',6''-tri-O-benzoyl-3',4'-dideoxykanamycin B,
1,3,2',6',2'',3''-hexa-N-benzyloxycarbonyl-3'-O-benzoyl-Aminoglycoside XK-88-5.

C. Per-N-Benzyloxycarbonyl-5-O-Thioformyl-Poly-O-Benzoyl Aminoglycosides

In a manner similar to that described in Preparation 1D(1) treat each of the per-N-benzyloxycarbonyl-poly-O-benzoyl aminoglycoside derivatives prepared in Preparation 4B with N,N-dimethyl-α-chloroformimidinium chloride (prepared by reaction of N,N-dimethylformamide and phosgene in benzene) in methylene chloride and pyridine cooled in ice, followed by treatment with dry hydrogen sulfide. Isolate and purify each of the resultant products in a manner similar to that described in Preparation 1D(1) to obtain the corresponding 5-O-thioformyl derivative thereof.

PREPARATION 5

POLY-N-BENZYLOXYCARBONYL-5-O-THIO-FORMYL-BIS-N,O-CARBONYL-POLY-O-BENZ-OYL AMINOGLYCOSIDES

A. Per-N-Benzyloxycarbonyl Aminoglycosides

In a manner similar to that described in Preparation 1A(1) treat each of the following aminoglycosides with excess benzyl chloroformate and potassium carbonate in aqueous methanol.

gentamicin $X_2$, Antibiotic G-418,
Antibiotic JI-20A, Antibiotic JI-20B.

Isolate and purify each of the resultant products in a manner similar to that described to obtain, respectively, 1,3,2′,3″-tetra-N-benzyloxycarbonylgentamicin $X_2$, 1,3,2′,3″-tetra-N-benzyloxycarbonyl-Antibiotic G-418, 1,3,2′,6′,3″-penta-N-benzyloxycarbonyl-Antibiotic JI-20A, 1,3,2′,6′,3″-penta-N-benzyloxycarbonyl-Antibiotic JI-20B.

B. Poly-N-Benzyloxycarbonylbis-N,O-Carbonyl Aminoglycosides

In a manner similar to that described in Preparation 1B(1) treat each of the per-N-benzyloxycarbonyl aminoglycosides prepared in Preparation 5A with sodium hydride in dimethylformamide. Isolate and purify each of the resultant products in a manner similar to that to obtain, respectively, 1,3-di-N-benzyloxycarbonyl-2′,3′;3″,4″-bis-N,O-carbonyl-gentamicin $X_2$, 1,3-di-N-benzyloxycarbonyl-2′,3′;3″,4″-bis-N,O-carbonyl-Antibiotic G-418, 1,3,2′-tri-N-benzyloxycarbonyl-4′,6′-O,N-carbonyl-3″,4″-N,O-carbonyl-Antibiotic JI-20A, 1,3,2′-tri-N-benzyloxycarbonyl-4′,6′-O,N-carbonyl-3″,4″-N,O-carbonyl-Antibiotic JI-20B.

C. Poly-N-Benzyloxycarbonylbis-N,O-Carbonyl-Poly-O-Benzoyl Aminoglycosides

In a manner similar to that described in Preparation 1C(1) treat each of the aminoglycoside derivatives prepared in Preparation 5B with excess benzoyl chloride in pyridine at room temperature, then evaporate and purify each of the resultant products in a manner similar to that described to obtain, respectively, 1,3-di-N-benzyloxycarbonyl-2′,3′;3″,4″-bis-N,O-carbonyl-4′,6′,2″-tri-O-benzoylgentamicin $X_2$, 1,3-di-N-benzyloxycarbonyl-2′,3′;3″,4″-bis-N,O-carbonyl-4′,6′,2″-tri-O-benzoyl-Antibiotic G-418, 1,3,2′-tri-N-benzyloxycarbonyl-4′,6′-O,N-carbonyl-3″,4″-N,O-carbonyl-3′,2″-di-O-benzoyl-Antibiotic JI-20A, 1,3,2′-tri-N-benzyloxycarbonyl-4′,6′-O,N-carbonyl-3″,4″-N,O-carbonyl-3′,2″-di-O-benzoyl-Antibiotic JI-20B.

D. Poly-N-Benzyloxycarbonyl-5-O-Thioformyl-Bis-N,O-Carbonyl-Poly-O-Benzoyl Aminoglycosides In a manner similar to that described in Preparation 1D(1) treat each of the aminoglycoside derivatives prepared in Preparation 5C with N,N-dimethyl-α-chloroformimidinium chloride (prepared by reaction of N,N-dimethylformamide and phosgene in benzene) followed by reaction with dry hydrogen sulfide. Isolate and purify each of the resultant products in a manner similar to that described to obtain the corresponding 5-O-thioformyl derivatives thereof.

PREPARATION 6

PER-N-BENZYLOXYCARBONYL-5-O-THIOFOR-MYL-POLY-O-BENZOYL-4″-O-ACETYLGEN-TAMICINS B AND $B_1$

A. Per-N-Benzyloxycarbonylgentamicins B and $B_1$

In a manner similar to that described in Preparation 1A(1) treat each of gentamicin B and gentamicin $B_1$ with an excess of benzyl chloroformate and potassium carbonate in aqueous methanol. Isolate each of the resultant products to obtain, respectively, 1,3,6′,3″-tetra-N-benzyloxycarbonylgentamicin B, and 1,3,6′,4″-tetra-N-benzyloxycarbonylgentamicin $B_1$.

B. Per-N-Benzyloxycarbonyl-4″-O-Acetylgentamicins B and $B_1$

1. To 1,3,6′,3″-tetra-N-benzyloxycarbonylgentamicin B (1 gm.) add a mixture of acetic anhydride (9 ml.) and concentrated hydrochloric acid (1 ml.). Stir at 25° C for 18 hours, then pour into water, extract the aqueous mixture with ethyl acetate, wash the combined ethyl acetate extracts with 5% aqueous sodium bicarbonate, then water. Dry the ethyl acetate solution over magnesium sulfate, filter and evaporate to a residue comprising 1,3,6′,3″-tetra-N-benzyloxycarbonyl-5,2′,3′,4′,2″-hexa-O-acetylgentamicin B, which is used without further purification in the procedure immediately following. 2. Dissolve 5 gms. of the per-N-benzyloxycarbonyl-per-O-acetylgentamicin B prepared in above procedure 6B(1) in 100 ml. of a solvent mixture comprising 10 ml. concentrated ammonium hydroxide and 90 ml. of methanol. Stir at room temperature for 70 hours, then evaporate in vacuo. Dissolve the resultant residue in chloroform, wash the chloroform solution with water, dry over magnesium sulfate and evaporate in vacuo to obtain 1,3,6′,3″-tetra-N-benzyloxycarbonyl-4″-O-acetylgentamicin B.

In similar manner treat 1,3,6′,3″-tetra-N-benzyloxycarbonylgentamicin $B_1$ with acetic anhydride and concentrated hydrochloric acid followed by treatment of the thereby formed 1,3,6′,3″-tetra-N-benzyloxycarbonyl-5,2′,3′,4′,2″,4″-hexa-O-acetylgentamicin $B_1$ with ammonia in methanol to obtain 1,3,6′,3″-tetra-N-benzyloxycarbonyl-4″-O-acetylgentamicin $B_1$.

C. 1,3,6′,3″-Tetra-N-Benzyloxycarbonyl-2′,3′,4′,2″-Tetra-O-Benzoyl-4″-O-Acetylgentamicins B and $B_1$ In a manner similar to that described in Preparation 1C(1) treat each of 1,3,6′,3″-tetra-N-benzyloxycarbonyl-4″-O-acetylgentamicin B and 1,3,6′,3″-tetra-N-benzyloxycarbonyl-4″-O-acetylgentamicin $B_1$ in dry pyridine with an excess of benzoyl chloride to obtain, respectively, 1,3,6′,3″-tetra-N-benzyloxycarbonyl-2′,3′,4′,2″-tetra-O-benzoyl-4″-O-acetylgentamicin B and 1,3,6′,3″-tetra-N-benzyloxycarbonyl-2′,3′, 4′,2″-tetra-O-benzoyl-4″-O-acetylgentamicin $B_1$.

D. 1,3,6′,3″-Tetra-N-Benzyloxycarbonyl-5-O-Thioformyl-2′,3′,4′,2″-Tetra-O-Benzoyl-4″-O-Acetylgentamicins B and $B_1$ In a manner similar to that described in Preparation 1D(1) treat each of the per-N-benzyloxycarbonyl-poly-O-benzoyl-4″-O-acetyl derivatives of gentamicins B and $B_1$ prepared as described in Preparation 6C with N,N-dimethyl-α-chloroformimidinium chloride (prepared by reaction of N-N-dimethylformamide and phosgene in benzene) followed by treatment with dry hydrogen sulfide, and isolate and purify each of the resultant products in a manner similar to that described to obtain, respectively, 1,3,6',3"-tetra-N-benzyloxycarbonyl-5-O-thioformyl-2',3',4',2"-tetra-O-benzoyl-4"-O-acetylgentamicin B, and 1,3,6',3"-tetra-N-benzyloxycarbonyl-5-O-thioformyl-2',3',4',2"-tetra-O-benzoyl-4"-O-acetylgentamicin $B_1$.

PREPARATION 7

TRI-N-BENZYLOXYCARBONYL-5-O-THIOFORMYL-POLY-O-BENZOYL-3",4"-N,O-CARBONYL-GENTAMICINS B AND $B_1$

A. 1,3,6'-Tri-N-Benzyloxycarbonylgentamicins B and $B_1$

To gentamicin B in dimethylsulfoxide (40 ml. per gram of gentamicin B) add cupric acetate (1 molar equivalents), stir for 30 minutes, then add dropwise a solution of N-(benzyloxycarbonyloxy)phthalimide (3.5 molar equivalents) in a minimum volume of tetrahydrofuran. Stir at room temperature for 1 hour, then add the reaction mixture to aqueous ammonia. Extract the reaction mixture with chloroform, evaporate the combined chloroform extracts in vacuo and chromatograph the resultant residue on silica gel eluting with the lower phase of a 2:1:1 chloroform:methanol:concentrated ammonium hydroxide system. Combine the like fractions containing the desired compound as determined by thin layer chromatography. Concentrate the eluates to a residue comprising 1,3,6'-tri-N-benzyloxycarbonylgentamicin B.

In the above procedure by utilizing gentamicin $B_1$ as starting aminoglycoside, there is obtained 1,3,6'-tri-N-benzyloxycarbonylgentamicin $B_1$.

B. 1,3,6'-Tri-N-Benzyloxycarbonyl-3",4"-N,O-Carbonylgentamicin B

Dissolve 1,3,6'-tri-N-benzyloxycarbonylgentamicin B in a minimum volume of dry tetrahydrofuran. Add N,N'-carbonyldiimidazole )1.05 molar equivalents) and allow the reaction mixture to stand at room temperature for several hours. Evaporate the reaction mixture, dissolve the resultant residue in a minimum volume of methanol, add the methanol to a large volume of dry ether, separate the resultant precipitate by filtration to obtain 1,3,6'-tri-N-benzyloxycarbonyl-3",4"-N,O-carbonylgentamicin B.

In similar manner, treat 1,3,6'-tri-N-benzyloxycarbonylgentamicin $B_1$ with N,N'-carbonyldiimidazole and tetrahydrofuran to obtain 1,3,6'-tri-N-benzyloxycarbonyl-3",4"-N,O-carbonylgentamicin $B_1$.

C. 1,3,6'-Tri-N-Benzyloxycarbonyl-2',3',4',2"-Tetra-O-Benzoyl-3",4"-N,O-Carbonylgentamicins B and $B_1$ In a manner similar to that described in Preparation 1C(1) treat each of 1,3,6'-tri-N-benzyloxycarbonyl-3",4"-N,O-carbonylgentamicin B and 1,3,6'-tri-N-benzyloxycarbonyl-3",4"-N,O-carbonylgentamicin $B_1$ in dry pyridine with an excess of benzoyl chloride to obtain, respectively, 1,3,6'-tri-N-benzyloxycarbonyl-2',3',4',2"-tetra-O-benzoyl-3",4"-N,O-carbonylgentamicin B and 1,3,6'-tri-N-benzyloxycarbonyl-2',3',4',2"-tetra-O-benzoyl-3",4"-N,O-carbonylgentamicin $B_1$.

D. 1,3,6'-Tri-N-Benzyloxycarbonyl-5-O-Thioformyl-2',3',4',2"-Tetra-O-Benzoyl-3",4"-N,O-Carbonylgentamicins B and $B_1$ In a manner similar to that descirbed in Preparation 1D(1) treat each of the tetra-N-benzyloxycarbonyl-poly-O-benzoyl-3",4"-N,O-carbonyl derivatives of gentamicins B and $B_1$ prepared in Preparation 7C with N,N-dimethyl-α-chloroformimidinium chloride (prepared by reaction of N,N-dimethylformamide and phosgene in benzene) followed by treatment with dry hydrogen sulfide in a manner similar to that described to obtain 1,3,6'-tri-N-benzyloxycarbonyl-5-O-thioformyl-2',3',4',2"-tetra-O-benzoyl-3",4"N,O-carbonylgentamicins B and $B_1$.

PREPARATION 8

PER-N-PROTECTED-PER-O-PROTECTED-1N-ALKYL-5-O-THIOFORMYLAMINOGLYCOSIDES

A. Per-N-Benzyloxycarbonyl-5-O-Thioformyl-poly-O-Benzoyl-1-N-Alkylaminoglycosides In the procedure of Preparations 4A through 4C, utilize as starting compounds the 1-N-ethyl, 1-N-propyl, and 1-N-(δ-aminobutyl) derivatives of each of the aminoglycoside starting compounds of Preparation 4A to obtain the corresponding 1-N-ethyl, 1-N-propyl, and 1-N-(δ-aminobutyl) derivatives, respectively, each of the per-N-benzyloxycarbonyl-5-O-thioformyl-poly-O-benzoylaminoglycoside products of Preparation 4C.

B. Poly-N-Benzyloxycarbonyl-5-O-Thioformyl-Bis-N,O-CarbonylPoly-O-Benzoyl-1-N-Alkylaminoglycosides In the procedure of Preparations 5A through 5D, utilize as starting compounds the 1-N-ethyl, 1-N-propyl, and 1-N-( δ-aminobutyl) derivatives of each of the aminoglycoside starting compounds of Preparation 5A to obtain, respectively, the corresponding 1-N-ethyl, 1-N- propyl, and 1-N-(δ-aminobutyl) derivatives of each of the poly-N-benzyloxycarbonyl-5-O-thioformyl-bis-N,O-carbonyl-poly-O-benzoylaminoglycoside products of Preparation 5D.

C. Per-N-Benzyloxycarbonyl-5-O-Thioformyl-Poly-O-Benzoyl-4"-O-Acetyl-1-N-Alkylgentamicins B and $B_1$ In the procedure of Preparations 6A through 6D, utilize as starting compounds the 1-N-ethyl, 1-N-propyl, and 1-N-(δ-aminobutyl) derivatives of each of the aminoglycoside starting compounds of Preparation 6A to obtain, respectively, the corresponding 1-N-ethyl, 1-N-propyl, and 1-N-(δ-aminobutyl) derivatives of each of the per-N-benzyloxycarbonyl-5-O-thioformyl-poly-O-benzoyl-4"-O-acetylgentamicin B and $B_1$ derivatives of Preparation 6D.

D. Per-N-Benzyloxycarbonyl-5-O-Thioformyl-Poly-O-Benzoyl-3",4"-N,O-Carbonyl-1-N-Alkylgentamicins B and $B_1$ In the procedure of Preparations 7A through 7D, utilize as starting compounds the 1-N-ethyl, 1-N-propyl, and 1-N-(δ-aminobutyl) derivatives of each of the aminoglycoside starting compounds of Preparation 7A to obtain, respectively, the corresponding 1-N-ethyl, 1-N-propyl, and 1-N-(δ-aminobutyl) derivatives of each of the per-N-benzyloxycarbonyl-5-O-thioformyl-poly-O-benzoyl-3",4"-N,O-carbonylgentamicin B and $B_1$ products of Preparation 7D.

PREPARATION 9

PER-N-PROTECTED-PER-O-PROTECTED-1,2'-DI-N-ALKYL-5-O-THIOFORMYLAMINO-GLYCOSIDES

A. Tetra-N-Benzyloxycarbonyl-5-O-Thioformyl-2"-O-Benzoyl-3",4"-N,O-Carbonyl-1,2'-Di-N-Alkylgentamicins In the procedure of Preparation 1 utilize as starting compounds the 1,2'-di-N-ethyl, 1,2'-di-N-propyl, and 1,2'-di-N-(δ-aminobutyl) derivatives of each of gentamicins $C_1$, $C_{1a}$, $C_2$, $C_{2a}$ and $C_{2b}$ to obtain, respectively, the corresponding 1,2'-di-N-ethyl, 1,2'-di-N-propyl, and 1,2'-di-N-(δ-aminobutyl) derivatives of each of the tetra-N-benzyloxycarbonyl-5-O-thioformyl-2''-O-benzoyl-3'',4''-N,O-carbonylaminoglycoside products of Preparation 1.

B. Tetra-N-Ethoxycarbonyl-5-O-Thioformyl-2''-O-Benzoyl-3'',4''-N,O-Carbonyl-1,2'-di-N-Alkylaminoglycosides In the procedure of Preparation 2 utilize as starting compounds the 1,2'-di-N-ethyl, 1,2'-di-N-propyl, and 1,2'-di-N-(δ-aminobutyl) derivatives of each of sisomicin, verdamicin, an Antibiotic G-52 to obtain, respectively, the corresponding 1,2'-di-N-ethyl, 1,2'-di-N-propyl, and 1,2'-di-N-(δ-aminobutyl)-aminoglycoside products of Preparation 2.

C. Poly-N-Benzyloxycarbonyl-5-O-Thioformyl-Bis-N,O-CarbonylPoly-O-Benzoyl-1,2'-Di-N-Alkylaminoglycosides In the procedure of Preparation 5 utilize as starting compounds the 1,2'-di-N-ethyl, 1,2'-di-N-propyl, and 1,2'-di-N-(δ-aminobutyl) derivatives of each of gentamicin $X_2$, Antibiotic G-418, Antibiotic JI-20A and Antibiotic JI-20B to obtain, respectively, the corresponding poly-N-benzyloxycarbonyl-5-O-thioformyl-bis-N,O-carbonyl-poly-O-benzoyl products of Preparation 5.

PREPARATION 10

PER-N-PROTECTED-PER-O-PROTECTED-5-O-THIOFORMYL-1,6'-DI-N-ALKYLAMINOGLYCOSIDES 1,3,2',6'-Tetra-N-Benzyloxycarbonyl-5-O-Thioformyl-2''-O-Benzoyl-3'',4''-N,O-Carbonyl-1-N-Alkylgentamicin $C_{1a}$ In the procedure of Preparation 1 utilize as starting compounds the 1,6'-di-N-ethyl, 1,6'-di-N-propyl, and 1,6'-di-N-(δ-aminobutyl) derivatives of gentamicin $C_{1a}$ to obtain, respectively, 1,3,2',6'-tetra-N-benzyloxycarbonyl-2''-O-benzoyl-3'',4''-N,O-carbonyl-5-O-thioformyl-1,6'-di-N-ethylgentamicin $C_{1a}$, 1,3,2',6'-tetra-N-benzyloxycarbonyl-2''-O-benzoyl-3'',4''-N,O-carbonyl-5-O-thioformyl-1,6'-di-N-propylgentamicin $C_{1a}$, 1,3,2',6'-tetra-N-benzyloxycarbonyl-2''-O-benzoyl-3'',4''-N,O-carbonyl-5-O-thioformyl-1,6'-di-N-(δ-benzyloxycarbonylaminobutyl)-gentamicin $C_{1a}$.

B. Tetra-N-Ethoxycarbonyl-5-O-Thioformyl-2''-O-Benzoyl-3'',4''-N,O-Carbonyl-1,6'-Di-N-Alkylaminoglycosides In the procedure of Preparation 2 utilize as starting compounds the 1,6'-di-N-ethyl, 1,6'-di-N-propyl, and 1,6'-di-N-(δ-aminobutyl) derivatives of sisomicin, verdamicin, Antibiotic 66-40B and Antibiotic 66-40D to obtain, respectively, the corresponding 1,6'-di-N-ethyl, 1,6'-di-N-propyl, and 1,6'-di-N-(δ-aminobutyl) derivatives of each of the tetra-N-ethoxycarbonyl-5-O-thioformyl-2''-O-benzoyl-3'',4''-N,O-carbonylaminoglycoside products of Preparation 2.

C. Per-N-Benzyloxycarbonyl-5-O-Thioformyl-Poly-O-Benzoyl-1,6'-Di-N-Alkyl-3',4'-Dideoxykanamycin B In the procedure of Preparation 4 utilize as starting compounds the 1,6'-di-N-ethyl, 1,6'-di-N-propyl, and 1,6'-di-N-(δ-aminobutyl) derivatives of 3',4'-dideoxykanamycin B to obtain, respectively, 1,3,2',6',3''-penta-N-benzyloxycarbonyl-5-O-thioformyl-2'',4'',6''-tri-O-benzoyl-1,6'-di-N-ethyl-3',4'-dideoxykanamycin B, 1,3,2',6',3''-penta-N-benzyloxycarbonyl-5-O-thioformyl-2'',4'',6''-tri-O-benzoyl-1,6'-di-N-propyl-3',4'-dideoxykanamycin B, 1,3,2',6',3''-penta-N-benzyloxycarbonyl-5-O-thioformyl-2'',4'',6''-tri-O-benzoyl-1,6'-di-N-(δ-benzyloxycarbonylaminobutyl)-3',4'-dideoxykanamycin B.

D. Per-N-Protected Per-O-Protected-5-O-Thioformyl-1,6'-di-N-Alkylgentamicin B

In the procedures of Preparations 6 and 7 utilize as starting compounds the 1,6'-di-N-ethyl, 1,6'-di-N-propyl, and 1,6'-di-N-(δ-aminobutyl) derivatives of gentamicin B to obtain, respectively, the corresponding 1,6'-di-N-ethyl, 1,6'-di-N-propyl, and 1,6'-di-N-(δ-aminobutyl)-derivatives of each of 1,3,6',3''-tetra-N-benzyloxycarbonyl-5-O-thioformyl-2',3',4',2''-tetra-O-benzoyl-4''-O-acetylgentamicin B and of 1,3,6'-tri-N-benzyloxycarbonyl-5-O-thioformyl-2',3',4',2''-tetra-O-benzoyl-3'',4''-N,O-carbonylgentamicin B.

EXAMPLE 1

5-DEOXYGENTAMICINS AND 1-N-ALKYL, 1,2'-DI-N-ALKYL AND 1,6'-DI-N-ALKYL DERIVATIVES THEREOF

A. 5-Deoxygentamicin $C_2$ 1. 1,3,2',6'-Tetra-N-Benzyloxycarbonyl-2''-Benzoyl-3'',4''-N,O-Carbonyl-5-Deoxygentamicin $C_2$ To 1,3,2',6'-tetra-N-benzyloxycarbonyl-5-O-thioformyl-2''-O-benzoyl-3'',4''-N,O-carbonylgentamicin $C_2$ (4.08 gms.) in dry toluene (80 ml.) under argon, add tri-n-butylstannane (3.0 gms.) and heat the reaction mixture at reflux temperature for 7 hours. Evaporate the reaction mixture in vacuo, then chromatograph the resultant residue on silica gel (250 gms.) eluting first with chloroform:dichloromethane (1:1) to remove the tin compounds, then elute with 1% methanol in chloroform. Monitor the fractions by thin layer chromatography on silica gel, eluting with 3% methanol in chloroform. Combine the like fractions containing the desired 5-deoxy derivative and evaporate. Dry the resultant residue at 60° C in vacuo to give 1,3,2',6'-tetra-N-benzyloxycarbonyl-2''-O-benzoyl-3'',4''-N,O-carbonyl-5-deoxygentamicin $C_2$, yield 3.22 gms. (78% theory); m.p. 103°–106° C, $[\alpha]_D^{26} + 117.1$ (chloroform, c=0.48).

2. 5-Deoxygentamicin $C_2$

To a solution of 1,3,2',6'-tetra-N-benzyloxycarbonyl-2''-O-benzoyl-3'',4''-N,O-carbonyl-5-deoxygentamicin $C_2$ (3.22 gms.) in dimethylsulfoxide (60 ml.) add potassium hydroxide (6 gms.) in water (12 ml.) and stir the reaction mixture under an atmosphere of nitrogen for 70 hours. Add water (200 ml.) to the reaction mixture, stir the solution with IRC-50 (H+) resin until all the aminoglycoside has been adsorbed onto the resin, pour the resin into a column, wash the column with water, then elute with 2 N ammonium hydroxide. Combine the like eluates containing the desired product as determined by thin layer chromatography and evaporate the combined eluates and chromatograph the resultant residue on a short silica gel column eluting with a chloroform: methanol:concentrated ammonium hydroxide mixture (2:1:0.3 v/v/v). Combine the like fractions containing the desired product as determined by thin layer chromatography, evaporate the combined fractions, add water to the residue and pass over a small quantity of IRA-401S (OH−) resin. Lyophilize the eluate to obtain 5-deoxygentamicin $C_2$ as a white amorphous solid, yield 0.913 gms. (61% theory), m.p. 84°–88° C, $[\alpha]_D^{26}$ + 187.3° (water, c=0.66).

B. 5-Deoxygentamicins $C_1$, $C_{1a}$, $C_{2a}$ and $C_{2b}$

In the procedure of Example 1A utilize as starting compounds the tetra-N-benzyloxycarbonyl-5-O-thioformyl-2″-O-benzoyl-3″,4″-N,O-carbonylgentamicin derivatives of Preparation 1D(2) to obtain, respectively,
  5-deoxygentamicin $C_1$,
  5deoxygentamicin $C_{1a}$,
  5-deoxygentamicin $C_{2a}$,
  5-deoxygentamicin $C_{2b}$.

C. 5-Deoxy-1-N-Alkylgentamicins

In the procedure of Example 1A utilize as starting compounds the 5-O-thioformyl-1-N-alkyl derivatives of gentamicins $C_1$, $C_{1a}$, $C_2$, $C_{2a}$ and $C_{2b}$ prepared in Preparation 8E to obtain, respectively,
  5-deoxy-1-N-ethylgentamicin $C_1$,
  5-deoxy-1-N-propylgentamicin $C_1$,
  5-deoxy-1-N-(δ-aminobutyl)gentamicin $C_1$,
  5-deoxy-1-N-ethylgentamicin $C_{1a}$,
  5-deoxy-1-N-propylgentamicin $C_{1a}$,
  5-deoxy-1-N-(δ-aminobutyl)gentamicin $C_{1a}$,
  5-deoxy-1-N-ethylgentamicin $C_2$,
  5-deoxy-1N-propylgentamicin $C_2$,
  5-deoxy-1-N-(δ-aminobutyl)gentamicin $C_2$,
  5-deoxy-1-N-ethylgentamicin $C_{2a}$,
  5-deoxy-1-N-propylgentamicin $C_{2a}$,
  5-deoxy-1-N-(δ-aminobutyl)gentamicin $C_{2a}$,
  5-deoxy-1-N-ethylgentamicin $C_{2b}$,
  5-deoxy-1-N-propylgentamicin $C_{2b}$,
  5-deoxy-1-N-(δ-aminobutyl)gentamicin $C_{2b}$.

D. 5-Deoxy-1,2′-Di-N-Alkylgentamicins

In the procedure of Example 1A utilize as starting compounds the 5-O-thioformyl-1,2′-di-N-alkyl derivatives prepared in Preparation 9A to obtain, respectively,
  5-deoxy-1,2′-di-N-ethylgentamicin $C_1$,
  5-deoxy-1,2′-di-N-propylgentamicin $C_1$,
  5-deoxy-1,2′-di-N-(δ-aminobutyl)gentamicin $C_1$,
  5-deoxy-1,2′-di-N-ethylgentamicin $C_{1a}$,
  5-deoxy-1,2′-di-N-propylgentamicin $C_{1a}$,
  5-deoxy-1,2′-di-N-(δ-aminobutyl)gentamicin $C_{1a}$,
  5-deoxy-1,2′-di-N-ethylgentamicin $C_2$,
  5-deoxy-1,2′-di-N-propylgentamicin $C_2$,
  5-deoxy-1,2′-di-N-(δ-aminobutyl)gentamicin $C_2$,
  5-deoxy-1,2′-di-N-ethylgentamicin $C_{2a}$,
  5-deoxy-1,2′-di-N-propylgentamicin $C_{2a}$,
  5-deoxy-1,2′-di-N-(δ-aminobutyl)gentamicin $C_{2a}$,
  5-deoxy-1,2′-di-N-ethylgentamicin $C_{2b}$,
  5-deoxy-1,2′-di-N-propylgentamicin $C_{2b}$,
  5-deoxy-1,2′-di-N-(δ-aminobutyl)gentamicin $C_{2b}$.

E. 5-Deoxy-1,6′-Di-N-Alkylgentamicin $C_{1a}$

In the procedure of Example 1A utilize as starting compound each of the 5-O-thioformyl-1,6′-di-N-alkylgentamicin $C_{1a}$ derivatives prepared in Preparation 10A to obtain, respectively,
  5-deoxy-1,6′-di-N-ethylgentamicin $C_{1a}$,
  5-deoxy-1,6′-di-N-propylgentamicin $C_{1a}$,
  5-deoxy-1,6′-di-N-(δ-aminobutyl)gentamicin $C_{1a}$.

EXAMPLE 2

5-DEOXYSISOMICIN AND OTHER 5-DEOXY-4′,5′-DEHYDROAMINOGLYCOSIDES

A. 5-Deoxysisomicin 1. 1,3,2′,6′-Tetra-N-Ethoxycarbonyl-2″-O-Benzoyl-3″,4″-N,O-Carbonyl-5-deoxysisomicin Dissolve 1,3,2′,6′-tetra-N-ethoxycarbonyl-5-O-thioformyl-2″-O-benzoyl-3″,4″-N,O-carbonylsisomicin (5.0 gms.) and tri-n-butylstannane (3.5 gms.) in dry toluene (90 ml.) and heat at reflux temperature for 15 hours under an atmosphere of argon. Evaporate the reaction mixture in vacuo, then wash the resultant residue twice by decantation with hexane and dissolve in chloroform. Apply the chloroform solution to a column of silica gel (6 × 30 cm.) containing from 2 to 3% calcium hydroxide. Elute the column with chloroform to remove the tin compounds, then develop the column with a 3% ethanol-chloroform solvent mixture, monitoring the fractions by thin layer chromatography (in 5% methanol:chloroform). Combine those fractions containing 1,3,2′,6′-tetra-N-ethoxycarbonyl-2″-O-benzoyl-3″,4″-N,O-carbonyl-5-deoxysisomicin, evaporate the combined fractions and dry the resultant residue at 60° C in vacuo to obtain 1,3,2′,6′tetra-N-ethoxycarbonyl-2″-O-benzoyl-3″,4″-N,O-carbonyl-5-deoxysisomicin, yield 2.6 gms. (56% theory), m.p. 160°–170° C (dec.); $[\alpha]_D^{26}$ + 122.0° (chloroform, c=0.32).

2. 5-Deoxysisomicin

To a solution of 1,3,2′,6′-tetra-N-ethoxycarbonyl-2″-O-benzoyl-3″,4″-N,O-carbonyl-5-deoxysisomicin (2.1 gms.) in dimethylsulfoxide (18 ml.) add potassium hydroxide (4 gms.) in water (6 ml.) and stir under an atmosphere of argon for two days. Add water (50 ml.) to the reaction mixture, stir the solution with IRC-50 (H+) resin until all the aminoglycoside has been adsorbed onto the resin, pour the resin onto the column, then elute with 2 N ammonium hydroxide. Combine the like eluates containing the desired product as determined by thin layer chromatography, evaporate the combined eluates, the chromatograph the resultant residue on silica gel (50 gms.) eluting with the lower phase of a chloroform:methanol:concentrated ammonium hydroxide (2:1:1) system. Combine the like fractions containing the desired product as determined by thin layer chromatography, evaporate the combined fractions, add water to the resultant residue and pass over a small quantity of IRA-401S (OH−) resin. Lyophilize the eluate to obtain 5-deoxysisomicin as a white amorphous solid, yield 0.697 gms. (59% theory).

B. 5-Deoxy-Antibiotic G-52, 5-Deoxy-Antibiotic 66-40B, 5-Deoxy-Antibiotic 66-40D and 5-Deoxyverdamicin In the procedure of Example 2A utilize as starting compounds the 5-O-thioformyl derivatives of Antibiotic G-52, Antibiotic 66-40B, Antibiotic 66-40D and of verdamicin prepared in Preparation 2D(2) to obtain, respectively,
  5-deoxy-Antibiotic G-52,
  5-deoxy-Antibiotic 66-40B,
  5-deoxy-Antibiotic 66-40D,
  5-deoxyverdamicin.

EXAMPLE 3

5-DEOXY-1-N-ALKYLSISOMICIN AND 5-DEOXY-1-N-ALKYL DERIVATIVES OF OTHER 4′,5′-DEHYDROAMINOGLYCOSIDES

A. 5-Deoxy-1-N-Alkylsisomicin 1. 1,3,2′,6′-Tetra-N-Benzyloxycarbonyl-2″-O-Benzoyl-3″,4″-N,O-Carbonyl-5-Deoxy-1N-Ethylsisomicin Dissolve 1,3,2′,6′-tetra-N-benzyloxycarbonyl-5-O-thioformyl-2″-O-benzoyl-3″,4″-N,O-carbonyl-1-N-ethylsisomicin (6.5 gms.) and tri-n-butylstannane (5 gms.) in dry toluene (200 ml.) and heat the solution at reflux temperature under an atmosphere of argon for 18 hours. Cool the reaction mixture and add slowly to well-stirred hexane (800 ml.) Separate the resultant precipitate by filtration, wash the precipitate with hexane and dry in vacuo to give 1,3,2',6'-tetra-N-benzyloxycarbonyl-2''-O-benzoyl-3'',4''-N,O-carbonyl-5-deoxy-1-N-ethylsisomicin, which is used without further purification in the procedure of Example 3A(2).

2. 5-Deoxy-1-N-Ethylsisomicin

To the 1,3,2',6'-tetra-N-benzyloxycarbonyl-2''-O-benzoyl-3'',4''-N,O-carbonyl-5-deoxy-1-N-ethylsisomicin prepared in above Example 3A(1) in dimethylsulfoxide (60 ml.) add a solution of potassium hydroxide (10 gms.) in water (50 ml.) and stir the reaction mixture at room temperature under an atmosphere of argon for 48 hours. Add water (40 ml.); then stir the reaction mixture under an atmosphere of argon at 105°–115° C for 60 hours. Dilute the reaction mixture with water, then stir the solution with IRC-50 (H+) resin until all the aminoglycoside has been adsorbed onto the resin. Pour the resin into a column, wash the column with water, then elute with 2 N ammonium hydroxide. Combine the like eluates containing the desired product as determined by thin layer chromatography, evaporate the combined eluates and chromatograph the resultant residue on silica gel (200 gms.) eluting with the lower phase of a 2:1:1 (v/v/v) chloroform: isopropanol:ammonium hydroxide (21%) mixture. Combine the like fractions containing 5-deoxy-1-N-ethylsisomicin as determined by thin layer chromatography, evaporate the combined fractions, add water to the resultant residue and pass the aqueous solution through a short column of IRA-401S (OH−) resin. Lyophilize the eluate to a residue of 5-deoxy-1-N-ethylsisomicin, yield 0.58 gms. (21% theory), m.p. 80°–84° C.

3. Other 5-Deoxy-1-N-Alkylsisomicins

In the procedure of Example 3A(1) and (2) utilize as starting compounds each of 1,3,2',6'-tetra-N-benzyloxycarbonyl-5-O-thioformyl-2''-O-benzoyl-3'',4''-N,O-carbonyl-1-N-(n-propyl)-sisomicin, and 1,3,2',6'-tetra-N-benzyloxycarbonyl-5-O-thioformyl-2''-O-benzoyl-3'',4''-N,O-carbonyl-1-N-(δ-benzyloxycarbonylaminobutyl)sisomicin to obtain, respectively, 5-deoxy-1-N-(n-propyl)sisomicin; 474 (MH+) 398, 217, 199, 189, 171, 160, 127, and 5-deoxy-1-N-(δ-aminobutyl)sisomicin; 503 (MH+) 246, 228, 218, 200, 160, 127.

B. Other 5-Deoxy-1-N-Alkylaminoglycosides

In the procedure of Example 3A(1) and (2) utilize as starting compounds the 5-O-thioformyl-1-N-alkyl derivatives of Antibiotic G-52, Antibiotic 66-40B, Antibiotic 66-40D and of verdamicin prepared as described in Preparation 3D(2) and (3) to obtain, respectively, 5-deoxy-1-N-ethyl-Antibiotic G-52,
5-deoxy-1-N-propyl-Antibiotic G-52,
5-deoxy-1-N-(δ-aminobutyl)-Antibiotic G-52,
5-deoxy-1-N-ethyl-Antibiotic 66-40B,
5-deoxy-1-N-propyl-Antibiotic 66-40B,
5-deoxy-1-N-(δ-aminobutyl)-Antibiotic 66-40B,
5-deoxy-1-N-ethyl-Antibiotic 66-40D,
5-deoxy-1-N-propyl-Antibiotic 66-40D,
5-deoxy-1-N-(δ-aminobutyl)-Antibiotic 66-40D,
5-deoxy-1-N-ethylverdamicin,
5-deoxy-1-N-propylverdamicin,
5-deoxy-1-N-(δ-aminobutyl)verdamicin.

EXAMPLE 4

5-DEOXYAMINOGLYCOSIDES,
5-DEOXY-1-N-ALKYLAMINOGLYCOSIDES,
5-DEOXY-1,2'-DI-N-ALKYLAMINOGLYCOSIDES, AND
5-DEOXY-1,6'-DI-N-ALKYLAMINOGLYCOSIDES

In a manner similar to that described in Examples 1–3 treat each of the per-N-protected-per-O-protected-5-O-thioformylaminoglycoside derivatives prepared in Preparations 4–10 with tri-n-butylstannane and dry toluene under an atmosphere of argon followed by treatment of the per-N-protected-per-O-protected-5-deoxyaminoglycoside thereby formed in dimethylsulfoxide with aqueous potassium hydroxide to obtain, respectively, 5-deoxygentamicin A, 5-deoxygentamicin $X_1$,
5-deoxykanamycin A, 5-deoxykanamycin B,
5-deoxykanamycin C, 5,3',4'-trideoxykanamycin B,
5-deoxy-Aminoglycoside XK-88-5, 5-deoxygentamicin $X_2$,
5-deoxy-Antibiotic G-418, 5-deoxy-Antibiotic JI-20A,
5-deoxy-Antibiotic JI-20B, 5-deoxygentamicin B,
5-deoxygentamicin $B_1$, 5-deoxy-1-N-ethylgentamicin A,
5-deoxy-1-N-propylgentamicin A,
5-deoxy-1N-(δ-aminobutyl)gentamicin A,
5-deoxy-1-N-ethylgentamicin $X_1$,
5-deoxy-1-N-propylgentamicin $X_1$,
5-deoxy-1-N-(δ-aminobutyl)gentamicin $X_1$,
5-deoxy-1-N-ethylkanamycin A,
5-deoxy-1-N-propylkanamycin A,
5-deoxy-1-N-(δ-aminobutyl)kanamycin A,
5-deoxy-1-N-ethylkanamycin B,
5-deoxy-1-N-propylkanamycin B,
5-deoxy-1-N-(δ-aminobutyl)kanamycin B,
5-deoxy-1-N-ethylkanamycin C,
5-deoxy-1-N-propylkanamycin C,
5-deoxy-1-N-(δ-aminobutyl)kanamycin C,
1-N-ethyl-5,3',4'-trideoxykanamycin B,
1-N-propyl-5,3',4'-trideoxykanamycin B,
1-N-(δ-aminobutyl)-5,3',4'-trideoxykanamycin B,
5-deoxy-1-N-ethyl-Antibiotic XK-88-5,
5-deoxy-1-N-propyl-Antibiotic XK-88-5,
5-deoxy-1-N-(δ-aminobutyl)-Antibiotic XK-88-5,
5-deoxy-1-N-ethylgentamicin $X_2$,
5-deoxy-1-N-propylgentamicin $X_2$,
5-deoxy-1-N-(δ-aminobutyl)gentamicin $X_2$,
5-deoxy-1-N-ethyl-Antibiotic G-418,
5-deoxy-1-N-propyl-Antibiotic G-418,
5-deoxy-1-N-(δ-aminobutyl)-Antibiotic G-418,
5-deoxy-1-N-ethyl-Antibiotic JI-20A,
5-deoxy-1-N-propyl-Antibiotic JI-20A,
5-deoxy-1-N-(δ-aminobutyl)-Antibiotic JI-20A, 5-deoxy-1-N-ethyl-Antibiotic JI-20B,
5-deoxy-1-N-propyl-Antibiotic JI-20B,
5-deoxy-1-N-(δ-aminobutyl)-Antibiotic JI-20B,
5-deoxy-1-N-ethylgentamicin B,
5-deoxy-1-N-propylgentamicin B,
5-deoxy-1-N-(δ-aminobutyl)gentamicin B,
5-deoxy-1-N-ethylgentamicin $B_1$,
5-deoxy-1-N-propylgentamicin $B_1$,
5-deoxy-1-N-(δ-aminobutyl)gentamicin $B_1$,
5-deoxy-1-N-ethylgentamicin $C_1$,
5-deoxy-1-N-propylgentamicin $C_1$, 5-deoxy-1-N-(δ-aminobutyl)gentamicin $C_1$,
5-deoxy-1-N-ethylgentamicin $C_{1a}$,
5-deoxy-1-N-propylgentamicin $C_{1a}$,
5-deoxy-1-N-(δ-aminobutyl)gentamicin $C_{1a}$,
5-deoxy-1-N-ethylgentamicin $C_2$,
5-deoxy-1-N-propylgentamicin $C_2$,
5-deoxy-1-N-(δ-aminobutyl)gentamicin $C_2$,
5-deoxy-1-N-ethylgentamicin $C_{2a}$,
5-deoxy-1-N-propylgentamicin $C_{2a}$,
5-deoxy-1-N-(δ-aminobutyl)gentamicin $C_{2a}$,
5-deoxy-1-N-ethylgentamicin $C_{2b}$,
5-deoxy-1-N-propylgentamicin $C_{2b}$,
5-deoxy-1-N-(δ-aminobutyl)gentamicin $C_{2b}$,
5-deoxy-1,2'-di-N-ethylgentamicin $C_1$,
5-deoxy-1,2'-di-N-propylgentamicin $C_1$,
5-deoxy-1,2'-di-N-(δ-aminobutyl)gentamicin $C_1$,
5-deoxy-1,2'-di-N-ethylgentamicin $C_{1a}$,
5-deoxy-1,2'-di-N-propylgentamicin $C_{1a}$,
5-deoxy-1,2'-di-N-(δ-aminobutyl)gentamicin $C_{1a}$, 5-deoxy-1,2'-di-N-ethylgentamicin $C_2$, 5-deoxy-1,2'-di-N-propylgentamicin $C_2$,
5-deoxy-1,2'-di-N-(δ-aminobutyl)gentamicin $C_2$,
5-deoxy-1,2'-di-N-ethylgentamicin $C_{2a}$,
5-deoxy-1,2'-di-N-propylgentamicin $C_{2a}$,
5-deoxy-1,2'-di-N-(δ-aminobutyl)gentamicin $C_{2a}$,
5-deoxy-1,2'-di-N-ethylgentamicin $C_{2b}$,
5-deoxy-1,2'-di-N-propylgentamicin $C_{2b}$,
5-deoxy-1,2'-di-N-(δ-aminobutyl)gentamicin $C_{2b}$,
5-deoxy-1,2'-di-N-ethylsisomicin,
5-deoxy-1,2'-di-N-propylsisomicin,
5-deoxy-1,2'-di-N-(δ-aminobutyl)sisomicin,
5-deoxy-1,2'-di-N-ethylverdamicin,
5-deoxy-1,2'-di-N-propylverdamicin,
5-deoxy-1,2'-di-N-(δ-aminobutyl)verdamicin,
5-deoxy-1,2'-di-N-ethyl-Antibiotic G-52,
5-deoxy-1,2'-di-N-propyl-Antibiotic G-52,
5-deoxy-1,2'-di-N-(δ-aminobutyl)-Antibiotic G-52,
5-deoxy-1,2'-di-N-ethylgentamicin $X_2$,
5-deoxy-1,2'-di-N-propylgentamicin $X_2$,
5-deoxy-1,2'-di-N-(δ-aminobutyl)gentamicin $X_2$,
5-deoxy-1,2'-di-N-ethyl-Antibiotic G-418,
5-deoxy-1,2'-di-N-propyl-Antibiotic G-418,
5-deoxy-1,2'-di-N-(δ-aminobutyl)-Antibiotic G-418,
5-deoxy-1,2'-di-N-ethyl-Antibiotic JI-20A, 5-deoxy-1,2'-di-N-propyl-Antibiotic JI-20A,
5-deoxy-1,2'-di-N-(δ-aminobutyl)-Antibiotic JI-20A,
5-deoxy-1,2'-di-N-ethyl-Antibiotic JI-20B,
5-deoxy-1,2'-di-N-propyl-Antibiotic JI-20B,
5-deoxy-1,2'-di-N-(δ-aminobutyl)-Antibiotic JI-20B,
5-deoxy-1,6'-di-N-ethylgentamicin $C_{1a}$,
5-deoxy-1,6'-di-N-propylgentamicin $C_{1a}$,
5-deoxy-1,6-di-N-(δ-aminobutyl)gentamicin $C_{1a}$,
5-deoxy-1,6'-di-N-ethylsisomicin,
5-deoxy-1,6'-di-N-propylsisomicin,
5-deoxy-1,6'-di-N-(δ-aminobutyl)sisomicin, 5-deoxy-1,6'-di-N-ethylverdamicin,
5-deoxy-1,6'-di-N-propylverdamicin,
5-deoxy-1,6'-di-N-(δ-aminobutyl)verdamicin,
5-deoxy-1,6'-di-N-ethyl-Antibiotic 66-40B,
5-deoxy-1,6'-di-N-propyl-Antibiotic 66-40B,
5-deoxy-1,6'-di-N-(δ-aminobutyl)-Antibiotic 66-40B,
5-deoxy-1,6'-di-N-ethyl-Antibiotic 66-40D,
5-deoxy-1,6'-di-N-propyl-Antibiotic 66-40D,
5-deoxy-1,6'-di-N-(δ-aminobutyl)-Antibiotic 66-40D,
1,6'-di-N-ethyl-5,3',4'-trideoxykanamycin B,
1,6'-di-N-propyl-5,3',4'-trideoxykanamycin B,
1,6'-di-N-(δ-aminobutyl)-5,3',4'-trideoxykanamycin B,
5-deoxy-1,6'-di-N-ethylgentamicin B,
5-deoxy-1,6'-di-N-propylgentamicin B,
5-deoxy-1,6'-di-N-(δ-aminobutyl)gentamicin B,
5-deoxy-1,6'-di-N-ethylgentamicin $B_1$,
5-deoxy-1,6'-di-N-propylgentamicin $B_1$,
5-deoxy-1,6'-di-N-(δ-aminobutyl)gentamicin $B_1$.

EXAMPLE 5

5-DEOXY-1-N-(AMINOHYDROXYALKANOYL)AMINOGLYCOSIDES

A. 3,6'-Di-N-Tert.-Butoxycarbonyl Derivatives of 5-Deoxygentamicins B and $B_1$ and of 5-Deoxykanamycin A 1. Add cupric acetate monohydrate (5.0 gms., 25 mmol) to a stirred solution of 5-deoxygentamicin B (4.82 gms., 10 mmol) in dimethylsulfoxide (250 ml.). Stir for 30 minutes, then to the cupric salt complex thereby formed in situ add dropwise a solution of carefully purified N-tert.-butoxycarbonyloxyphthalimide (5.79 gms., 22 mmol) in dimethylsulfoxide (20 ml.). Stir at room temperature for 6 hours, then pour the reaction mixture into 1.5 l. of stirred ether. Stir for 30 minutes, allow the reaction mixuture to stand, decant the supernatant solution, again add 500 ml. of ether to the residue, let stand and decant the supernatant solution. Dissolve the resultant residue in 100 ml. of methanol and bubble hydrogen sulfide for 15 minutes. Remove the cupric sulfide solid by filtration through a pad of Celite and wash the residue with methanol. Treat the methanolic solution with Amberlite IRA-401S ($OH^-$) ion exchange resin to bring the pH of the solution to about 8.5 – 9.0, remove the solids by filtration and wash the solids with methanol. Evaporate the solution to near dryness and lyophilize from water. Crystallize 3,6'-di-N-tert.-butoxycarbonyl-5-deoxygentamicin B by triturating with ether.

2. Treat 5-deoxygentamicin $B_1$ and 5-deoxykanamycin A in a manner similar to that described in Example 5A(1) to obtain 3,6'-di-N-tert.-butoxycarbonyl-5-deoxygentamicin $B_1$ and 3,6'-di-N-tert.-butoxycarbonyl-5-deoxykanamycin A, respectively.

B. 1-N-(Aminohydroxyalkyl)-3,6'-di-N-Tert.-Butoxycarbonyl Derivatives of 5-Deoxygentamicins B and $B_1$ and of 5-Deoxykanamycin A 1. Add to a stirring solution of 3,6'-di-N-tert.-butoxycarbonyl-5-deoxygentamicin B (11.28 g., 16.4 mmol) in methanol (100 ml.) and water (100 ml.), a solution of N-(S-β-benzyloxycarbonylamino-α-hydroxypropionyloxy)succinimide (10 g., 30 mmol) in 40 ml. of N,N-dimethylformamide over a fifteen minute period. After a period of two hours, evaporate off the solvents in vacuo at 50° C. Chromatograph the resultant residue on 500 g. of silica gel using a 30:10:0.5 ratio of chloroform:methanol:concentrated ammonium hydroxide to obtain 1-N-(S-β-benzyloxycarbonylamino-α-hydroxypropionyl)-3,6'-di-N-tert.-butoxycarbonyl-5-deoxygentamicin B.

2. Treat each of 3,6'-di-N-tert.-butoxycarbonyl-5deoxygentamicin $B_1$ and 3,6'-di-N-tert.-butoxycarbonyl-5-deoxykanamycin A in a manner similar to that described in above Example 5B(1) to obtain, respectively 1-N-(S-β-benzyloxycarbonylamino-α-hydroxypropionyl)-3,6'-di-N-tert.-butoxycarbonyl-5-deoxygentamicin $B_1$ and 1-N-(S-β-benzyloxycarbonylamino-α-hydroxypropionyl)-3,6'-di-N-tert.-butoxycarbonyl-5-deoxykanamycin A.

3. In the procedure of Example 5B(1) and (2) substitute for N-(S-β-benzyloxycarbonylamino-α-hydroxypropionyloxy)-succinimide other succinimide reagents such as N-(R-β-benzyloxycarbonylamino-α-hydroxypropionyloxy)succinimide, N-(S-γ-benzyloxycarbonylamino-α-hydroxybutyryloxy)succinimide, N-(R-γ-benzyloxycarbonylamino-α-hydroxybutyryloxy)succinimide, N-(S-δ-benzyloxycarbonylamino-α-hydroxyvaleryloxy)succinimide, and N-(R-δ-benzyloxycarbonylamino-α-hydroxyvaleryloxy)succinimide to obtain, respectively, 1-N-(R-β-benzyloxycarbonylamino-α-hydroxypropionyl)-3,6'-di-N-tert.-butoxycarbonyl-5-deoxygentamicin B, 1-N-(S-δ-benzyloxycarbonylamino-α-hydroxybutyryl)-3,6'-di-N-tert.-butoxycarbonyl-5-deoxygentamicin B, 1-N-(R-γ-benzyloxycarbonylamino-αhydroxybutyryl)-3,6'-di-N-tert.-butoxycarbonyl-5-deoxygentamicin B, 1-N-(S-δ-benzyloxycarbonylamino-α-hydroxyvaleryl)-3,6'-di-N-tert.-butoxycarbonyl-5-deoxygentamicin B, and 1-N-(R-δ-benzyloxycarbonylamino-α-hydroxyvaleryl)-3,6'-di-N-tert.-butoxycarbonyl-5-deoxygentamicin B, 1-N-(R-β-benzyloxycarbonylamino-α-hydroxypropionyl)-3,6'-di-N-tert.-butoxycarbonyl-5-deoxygentamicin $B_1$, 1-N-(S-γ-benzyloxycarbonylamino-α-hydroxybutyryl)-3,6'-di-N-tert.-butoxycarbonyl-5-deoxygentamicin $B_1$, 1-N-(R-γ-benzyloxycarbonylamino-α-hydroxybutyryl)-3,6'-di-N-tert.-butoxycarbonyl-5-deoxygentamicin $B_1$, 1-N-(S-δ-benzyloxycarbonylamino-60 -hydroxyvaleryl)-3,6'-di-N-tert.-butoxycarbonyl-5-deoxygentamicin $B_1$, and 1-N-(R-δ-benzyloxycarbonylamino-α-hydroxyvaleryl)-3,6'-di-N-tert.-butoxycarbonyl-5-deoxygentamicin $B_1$, 1-N-(R-β-benzyloxycarbonylamino-α-hydroxypropionyl)-3,6'-di-N-tert.-butoxycarbonyl-5-deoxykanamycin A, 1-N-(S-γ-benzyloxycarbonylamino-α-hydroxybutyryl)-3,6'-di-N-tert.-butoxycarbonyl-5-deoxykanamycin A, 1-N-(R-γ-benzyloxycarbonylamino-α-hydroxybutyryl)-3,6'-di-N-tert.-butoxycarbonyl-5-deoxykanamycin A, 1-N-(S-δ-benzyloxycarbonylamino-α-hydroxyvaleryl)-3,6'-di-N-tert.-butoxycarbonyl-5-deoxykanamycin A, and 1-N-(R-δ-benzyloxycarbonylamino-α-hydroxyvaleryl)-3,6'-di-N-tert.-butoxycarbonyl-5-deoxykanamycin A.

C. 5-Deoxy-1-N-(Aminohydroxyalkanoyl)aminoglycosides 1. 1-N-(S-β-Amino-α-Hydroxypropionyl)-5-Deoxygentamicin B Hydrogenate the product of Example 5B(1) at 50 psi at room temperature in a mixture of water (730 ml.) and methanol (240 ml.) in the presence of 5% palladium-on-charcoal catalyst (0.7 gms.) for 24 hours. Remove the catalyst by filtration through a pad of Celite and wash with water. Concentrate the combined filtrates and dry the residue thoroughly. Dissolve the residue in trifluoroacetic acid (80 ml.) and set aside for three minutes. Pour the solution into excess ether (2liters) to precipitate the trifluoroacetic acid salt of 1-N-(S-β-amino-α-hydroxypropionyl)-5-deoxygentamicin B. Isolate by filtration, wash with ether and dry. Dissolve the residue in water and treat with Amberlite IRA-401S (OH−) resin to bring to pH 9. Filter the solution, wash the resin and lyophilize the combined solution to give 1-N-(S-β-amino-α-hydroxypropionyl)-5-deoxygentamicin B.

2. In a manner similar to that described in above Example 5C(1) hydrogenate each of the intermediates prepared in Example 5B(2) and 5B(3) and isolate and purify each of the resultant products to obtain, respectively, 1-N-(S-β-amino-α-hydroxypropionyl)-5-deoxygentamicin $B_1$, 1-N-(S-β-amino-α-hydroxypropionyl)-5-deoxykanamycin A, 1-N-(R-β-amino-α-hydroxypropionyl)-5-deoxygentamicin B, 1-N-(R-β-amino-α-hydroxypropionyl)-5-deoxygentamicin $B_1$, 1-N-(R-β-amino-α-hydroxypropionyl)-5-dexoykanamycin A, 1-N-(S-γ-amino-α-hydroxybutyryl)-5-deoxygentamicin B, 1-N-(S-γ-amino-α-hydroxybutyryl)-5-deoxygentamicin $B_1$, 1-N-(S-γ-amino-α-hydroxybutyryl)-5-deoxykanamycin A, 1-N-(R-γ-amino-α-hydroxybutyryla-5-deoxygentamicin B, 1-N-(R-γ-amino-α-hydroxybutyryl)-5-deoxygentamicin $B_1$, 1-N-(R-γ-amino-α-hydroxybutyl)-5-dexoykanamycin A, 1-N-(S-δ-amino-α-hydroxyvaleryl)-5-deoxygentamicin B, 1-N-(S-δ-amino-α-hydroxyvaleryl)-5-deoxygentamicin $B_1$, 1-N-(S-δ-amino-α-hydroxyvaleryl)-5-deoxykanamycin A, 1-N-(R-δ-amino-α-hydroxyvaleryl)-5-deoxygentamicin B, 1-N-(R-δ-amino-α-hydroxyvaleryl)-5-deoxygentamicin $B_1$, 1-N-(R-δ-amino-αhydroxyvaleryl)-5-deoxykanamycin A.

EXAMPLE 6

5-DEOXYTOBRAMYCIN

1. When the requisite 5-O-thioformyl intermediate is prepared by reacting tobramycin with an excess of benzoyl chloroformate and potassium carbonate in aqueous methanol in a manner similar to that described in Preparation 1A(1) followed by reaction of the thereby formed 1,3,2',6',3''-penta-N-benzyloxycarbonyltobramycin with benzoyl chloride in pryidine in the manner of Preparation 1C(1) thence reaction of the resulting 1,3,2',6',3''-penta-N-benzyloxycarbonyl-4',2'',4'',6''-tetra-O-benzoyltobramycin with N,N-dimethyl-α-chloroformimidinium chloride in methylene chloride in pyridine followed by treatment with dry hydrogen sulfide in a manner similar to that described in Preparation 1D(1) whereby is obtained 1,3,2',6',3''-penta-N-benzloxycarbonyl-5-O-thioformyl-4',2'',4'',6''-tetra-O-benzoyltobramycin.

2. Treat 1,3,2',6',3''-penta-N-benzyloxycarbonyl-5-O-thioformyl-4',2'',4'',6''-tetra-O-benzoyltobramycin with tri-n-butylstannane and dry toluene under an atmosphere of argon followed by treatment of the 1,3,2',6',3''-penta-N-benzyloxycarbonyl-4',2'',4'',6''-tetra-O-benzoyl-5-deoxytobramycin thereby formed in dimethylsulfoxide with aqueous potassium hydroxide to obtain 5-deoxytobramycin.

EXAMPLE 7

ACID ADDITION SALTS

A. Dissolve 5 gms. of 5-deoxygentamicin $C_2$ in 25 ml. of water and adjust the pH of the solution to 4.2 with 1 N sulfuric acid. Pour into 300 ml. of methanol with vigorous agitation, continue the agitation for about 10–20 minutes, then filter. Wash the precipitate with methanol and dry at about 60° C in vacuo to obtain 5-deoxygentamicin $C_2$ sulfate.

B. In like manner the sulfate salt of the compounds of Examples 1–6 are prepared.

C. In the procedure of Example 6A, by substituting other acids for sulfuric acid, there is obtained the corresponding 5-deoxygentamicin $C_2$ acid addition salt.

The present invention includes within its scope pharmaceutical compositions comprising our novel 5-deoxy-4,6-di-O-(aminoglycosyl)-1,3-diaminocyclitols with a compatible, pharmaceutically acceptable carrier or coating. Also included within our invention is the method of eliciting an antibacterial response in a warm-blooded animal having a susceptible bacterial infection which comprises administering to said animal a non-toxic, antibacterially effective amount of a member selected from the group consisting of a 5-deoxygentamicin A, 5-deoxygentamicin B, 5-deoxygentamicin $B_1$, 5-deoxygentamicin $C_1$, 5-deoxygentamicin $C_{1a}$, 5-deoxygentamicin $C_2$, 5-deoxygentamicin $C_{2a}$, 5-deoxygentamicin $C_2b$, 5-deoxygentamicin $X_1$, 5-deoxygentamicin $X_2$, 5-deoxyverdamicin, 5-deoxytobramcin, 5-deoxy-Antibiotic G-418, 5-deoxy-Antibiotic 66-40B, 5-deoxy-Antibiotic 66-40D, 5-deoxy-Antibiotic JI-20A, 5-deoxy-Antibiotic JI-20B, 5-deoxy-Antibiotic G-52, 5-deoxykanamycin A, 5-deoxykanamycin B, 5-deoxykanamycin C, 5,3',4'-trideoxykanamycin B and 5-deoxy-Aminoglycoside XK-885;

the 1-N-X derivatives thereof wherein X is a substituent selected from the group consisting of —$CH_2Z$ and

wherein Z is a member selected from the group consisting of hydrogen, alkyl, alkenyl, cycloalkyl, cycloalkylalkyl, hydroxyalkyl, aminoalkyl, N-alkylaminoalkyl, aminohydroxyalkyl, N-alkylaminohydroxyalkyl, phenyl, benzyl, and tolyl, said substituent X having up to 7 carbon atoms and, when substituted by amino hydroxy, bearing the substituents on different carbon atoms;

the 2'-N-$CH_2Z$, 6'-N-$CH_2Z$, 1,2'-di-N-$CH_2Z$ and the 1,6'-di-N-$CH_2Z$ derivatives thereof wherein Z is as hereinabove defined;

and the pharmaceutically acceptable acid addition salts thereof.

As discussed hereinabove, the 5-deoxy-4,6-di-O-(aminoglycosyl)-1,3-diaminocyclitols of this invention and the non-toxic, pharmaceutically acceptable acid addition salts thereof are broad spectrum antibacterial agents which, advantageously, exhibit activity against organisms resistant to their 5-hydroxy precursors. Thus, the 5-deoxy compounds of this invention can be used alone or in combination with other antibiotic agents to prevent the growth or reduce the number of bacteria in various environments. They may be used, for example, to disinfect laboratory glassware, dental and medical equipment contaminated with Staphylococcus aureus or other bacteria inhibited by the 5-deoxy-derivatives of this invention. The activity of the 5-deoxy-4,6-di-O-(aminoglycosyl)-1,3-diaminocyclitols against gram negative bacteria renders them useful for combating infections caused by gram negative organisms, e.g. species of Proteus and Pseudomonas. Our 5-deoxy-4,6-di-O-(aminoglycosyl)-1,3-diaminocyclitols, e.g. 5-deoxygentamicin $C_2$ and 5-deoxyverdamicin have veterinary applications, particularly in the treatment of mastitis in cattle and Salmonella induced diarrhea in domestic animals such as the dog and the cat.

In general, the dosage administered of the 5-deoxy-4,6-di-O-(aminoglycosyl)-1,3-diaminocyclitols will be dependent upon the age and weight of the animal species being treated, the mode of administration, and the type and severity of bacterial infection being prevented or reduced. In general, the dosage of 5-deoxy-4,6-di-O-(aminoglycosyl)-1,3-diaminocyclitols employed to combat a given bacterial infection will be similar to the dosage requirements of the corresponding 5-hydroxy-4,6-di-O-(aminoglycosyl)-1,3-diaminocyclitol. Additionally, the 5-deoxy-4,6-di-O-(aminoglycosyl)-1,3-diaminocyclitols, particularly the 4-O-aminoglycosyl-6-O-garosaminyl-2,5-dideoxystreptamines, e.g. 5-deoxygentamicin $C_2$, are also advantageously cidal against certain acetylating organisms which are resistant to the 5-hydroxy precursors.

The 5-deoxy-4,6-di-O-(aminoglycosyl)-1,3-diaminocyclitols and the pharmaceutically acceptable acid addition salts thereof may be administered orally. They may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example such substances as water, fats, waxes, polyesters, polyols and the like.

For oral administration the 5-deoxy-4,6-di-O-(aminoglycosyl)-1,3-diaminocyclitol antibacterials of this invention may be compounded in the form of tablets, capsules, elixirs or the like or may even be admixed with animal feed. It is in these dosage forms that the antibacterials are most effective for treating bacterial infections of the gastrointestinal tract which infections cause diarrhea. They are also useful for pre- and post- operative gut sterilization.

In general, the topical preparations will contain from about 0.1 to about 3.0 gms. of 5-deoxy-4,6-di-O-(aminoglycosyl)-1,3-diaminocyclitols per 100 gms. of ointment, creams or lotion. The topical preparations are usually applied gently to lesions from about 2 to about 5 times a day.

The antibacterials of this invention may be utilized in liquid form such as solutions, suspensions and the like for otic and optic use and may also be administered parenterally via intramuscular, intravenous, subcutaneous and intrasternal injection. The injectable solution or suspension will usually be administered at from about 1 mg. to about 10 mgs. of anitbacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the anitbacterial agents of this invention and their derivatives may be employed:

Formulation 1

| Tablet | 10 mg. Tab. | 25 mg. Tab. | 100 mg. Tab. |
|---|---|---|---|
| | * | * | * |
| 5-deoxygentamicin $C_2$ | 10.5 mg. | 26.25 mg. | 105.0 mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

* 5% excess

Procedure

Prepare a slurry consisting of the 5-deoxygentamicin $C_2$ lactose and polyvinylpyrrolidone. Spray dry the slurry. Add the corn starch and magnesium stearate. Mix and compress into tablets.

Formulation 2

| Ointment | |
|---|---|
| 5-deoxygentamicin $C_2$ | 1.9 gm. |
| Methyl paraben U.S.P. | 0.5 gm. |
| Propyl paraben U.S.P. | 0.1 gm. |
| Petrolatum | to 1000 gm. |

Procedure

1. Melt the petrolatum.
2. Mix the 5-deoxygentamicin $C_2$, methylparaben and propylparaben with about 10% of the molten petrolatum.
3. Pass the mixture through a colloid mill.
4. Add the remainder of the petrolatum with agitation and cool the mixture until it becomes semi-solid. At this stage the product may be put into suitable containers.

Formulation 3

| Injectable Solution | Per 2.0 ml. vial | Per 50 Liters |
|---|---|---|
| 5-deoxygentamicin $C_2$ | 84* mgs. | 2100* gms. |
| Methyl paraben, U.S.P. | 3.6 mgs. | 90.0 gms. |
| Propyl paraben, U.S.P. | 0.4 mgs. | 10.0 gms. |
| Sodium bisulfite, U.S.P. | 6.4 mgs. | 160.0 gms. |
| Disodium Ethylenediamine tetraacetate dihydrate, R.G. | 0.2 mgs. | 5.0 gms. |
| Water, U.S.P. q.a. | 2.0 ml. | 50.0 liters |

*Includes a 5% manufacturing overcharge.

Procedure

For a 50.0 liter batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°–30° C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 5-deoxygentamicin $C_2$ sulfate. Bring the batch volume up to 50.0 liters with water for injection and agitate until homogeneous.

Under sterile conditions, filter the solution through a suitable bacteria retentive filter collecting the filtrate in a filling tank.

Fill the filtrate aseptically into sterile pyrogen-free multiple dose vials, stopper and seal.

In like manner, injectable solutions of other 5-deoxy-4,6-di-O-(aminoglycosyl)-1,3-diaminocyclitols and especially acid addition salts of such antibacterial agents, may be prepared by substituting an equivalent quantity of such compounds for 5-deoxygentamicin $C_2$ sulfate and by following the procedure set forth above.

We claim:

1. A 5-deoxy-4,6-di-O-(aminoglycosyl)-1,3-diaminocyclitol selected from the group consisting of
   5-deoxygentamicin B,
   5-deoxygentamicin $B_1$,
   5-deoxygentamicin $C_{1a}$,
   5-deoxygentamicin $C_2$,
   5-deoxygentamicin $C_{2a}$,
   5-deoxygentamicin $X_1$,
   5-deoxygentamicin $X_2$,
   5-deoxy-Antibiotic 66-40B,
   5-deoxy-Antibiotic 66-40D,
   5-deoxy-Antibiotic G-418,
   5-deoxy-Antibiotic JI-20A,
   5-deoxy-Antibiotic JI-20B,
   5-deoxyverdamicin,
   5-deoxykanamycin B,
   5-deoxykanamycin C,
   5,3',4'-trideoxykanamycin B,
   5-deoxy-Aminoglycoside XK-88-5,
   5-deoxytobramcyin;
   the 1-N-X derivatives thereof wherein X is a substituent selected from the group consisting of —$CH_2Z$ and

wherein Z is a member selected from the group consisting of hydrogen, alkyl, alkenyl, cycloalkyl, cycloalkylalkyl, hydroxyalkyl, aminoalkyl, alkylaminoalkyl, aminohydroxyalkyl, alkylaminohydroxyalkyl, phenyl, benzyl, and tolyl, said substituent Z having up to 7 carbon atoms and, when substituted by amino and hydroxy, bearing the substituents on different carbon atoms;
   the 2'-N-$CH_2Z$, 6'-N-$CH_2Z$, 1,2'-di-N-$CH_2Z$ and the 1,6'-di-N-$CH_2Z$ derivatives thereof wherein Z is as hereinabove defined;
   5-deoxy-Antibiotic G-52 and the 1-N-X derivatives thereof wherein X is as hereinabove defined;
   and the pharmaceutically acceptable acid addition salts thereof.

2. A compound of claim 1 which is a 4-O-aminoglycosyl-6-O-garosaminyl-2,5-dideoxystreptamine.

3. A compound of claim 1 which is a 1-N-X-4-O-aminoglycosyl-6-O-garosaminyl-2,5-dideoxystreptamine wherein X is a —$CH_2Z$ substituent selected from the group consisting of ethyl, propyl, and δ-aminobutyl.

4. A compound of claim 2 which is 5-deoxygentamicin $C_2$.

5. A compound of claim 1 which is a 1-N-X-4-O-aminoglycosyl-6-O-garosaminyl-2,5-dideoxystreptamine wherein X is a

substituent selected from the group consisting of 3-amino-2-hydroxypropionyl, 4-amino-2-hydroxybutyryl, and 5-amino-2-hydroxyvaleryl.

6. A compound of claim 5 which is a 1-N-X derivative of 5-deoxygentamicin B selected from the group consisting of 1-N-(3-amino-2-hydroxypropionyl)-5-deoxygentamicin B, 1-N-(4-amino-2-hydroxybutyryl)-5-deoxygentamicin B, and 1-N-(5-amino-2-hydroxyvaleryl)-5-deoxygentamicin B.

7. A compound of claim 5 which is a 1-N-X derivative of 5-deoxygentamicin $B_1$ selected from the group consisting of 1-N-(3-amino-2-hydroxypropionyl)-5-deoxygentamicin $B_1$, 1-N-(4-amino-2-hydroxybutyryl)-5-deoxygentamicin $B_1$, and 1-N-(5-amino-2-hydroxyvaleryl)-5-deoxygentamicin $B_1$.

8. A compound of claim 1 which is a 1,2'-di-N-$CH_2Z$-4-O-aminoglycosyl-6-O-garosaminyl-2,5-dideoxystreptamine wherein $CH_2Z$ is ethyl, propyl, or δaminobutyl.

9. A compound of claim 1 which is a 1,6'-di-N-$CH_2Z$-4-O-aminoglycosyl-6-O-garosaminyl-2,5-dideoxystreptamine wherein $CH_2Z$ is ethyl, propyl, or δ-aminobutyl.

10. The process for the preparation of a 5-deoxy-4,6-di-O-(aminoglycosyl)-1,3-diaminocyclitol which comprises the reaction of the corresponding 5-O-thioformyl-4,6-di-O-(aminoglycosyl)-1,3-diaminocyclitol having all amino functions protected by an amino protecting group, Y, and all primary and secondary hydroxyl groups protected by a hydroxy protecting group, R; with at least a molar equivalent of an organotin hydride in an inert aprotic solvent at a temperature of at least about 100° C and under an inert atmosphere; followed by removal of said amino protecting groups, Y, and said hydroxyl protecting groups R.

11. The process of claim 10 wherein said organotin hydride is tri-n-butylstannane.

12. The process of claim 10 wherein said organotin hydride is tri-n-butylstannane, said 5-thioformyl-4,6di-O-(aminoglycosyl)-1,3-diaminocyclitol is a 5-thioformyl-4-O-aminoglycosyl-6-O-garosaminyl-2-deoxystreptamine having all amino functions protected by benzyloxycarbonyl or ethoxycarbonyl groups, and all primary and secondary hydroxy groups protected by a member selected from the group consisting of benzoyl, acetyl and carbonyl derivatives of neighboring hydroxyl and amino groups.

13. The process of claim 10 for the preparation of 5-deoxysisomicin and 1-N-X derivatives thereof wherein X is a member selected from the group consisting of ethyl, propyl, and δ-aminobutyl, which comprises the reaction of 1,3,2',6'tetra-N-ethoxycarbonyl-5-O-thioformyl-2''-O-benzoyl-3'',4''-N,O-carbonylsisomicin or a 1-N-X' derivative thereof wherein X' is ethyl, propyl, or amino-protected δ-aminobutyl, with at least a molar equivalent of tri-n-butylstannane in refluxing toluene under an atmosphere of argon followed by treatment of the 1,3,2',6'-tetra-N-ethoxycarbonyl-2''-O-benzoyl-3'',4''-N,O-carbonyl-5-deoxysisomicin or 1-N-X' derivative thereof thereby formed with potassium hydroxide.

14. The method of eliciting an antibacterial response in a warm-blooded animal having a susceptible bacterial infection which comprises administering to said animal a non-toxic, antibacterially effective amount of a member selected from the group consisting of a 5-deoxy-4,6-di-O-(aminoglycosyl)-1,3-diaminocyclitol selected from the group consisting of 5-deoxygentamicin B,
5-deoxygentamicin $B_1$,
5-deoxygentamicin $C_{1a}$,
5-deoxygentamicin $C_2$,
5-deoxygentamicin $C_{2a}$,
5-deoxygentamicin $X_1$,
5-deoxygentamicin $X_2$,
5-deoxy-Antibiotic 66-40B,
5-deoxy-Antibiotic 66-40D,
5-deoxy-Antibiotic G-418,
5-deoxy-Antibiotic JI-20A,
5-deoxy-Antibiotic JI-20B,
5-deoxyverdamicin,
5-deoxykanamycin B,
5-deoxykanamycin C,
5,3',4'-trideoxykanamycin B,
5-deoxy-Aminoglycoside XK-88-5,
5-deoxytobramycin;

the 1-N-X derivatives thereof wherein X is a substituent selected from the group consisting of —$CH_2Z$ and

wherein Z is a member selected from the group consisting of hydrogen, alkyl, alkenyl, cycloalkyl, cycloalkylalkyl, hydroxyalkyl, aminoalkyl, alkylaminoalkyl, aminohydroxyalkyl, alkylaminohydroxyalkyl, phenyl, benzyl, and tolyl, said substituent Z having up to 7 carbon atoms and, when substituted by amino and hydroxy, bearing the substituents on different carbon atoms;

the 2'-N-$CH_2Z$, 6'-N-$CH_2Z$, 1,2'-di-N-$CH_2Z$ and the 1,6'-di-N-$CH_2Z$ derivatives thereof wherein Z is as hereinabove defined;

5-deoxy-Antibiotic G-52 and the 1-N-X derivatives thereof wherein X is as hereinabove defined;

and the pharmaceutically acceptable acid addition salts thereof.

15. A pharmaceutical composition comprising an antibacterially effective amount of a member selected from the group consisting of a 5-deoxy-4,6-di-O-(aminoglycosyl)-1,3-diaminocyclitol selected from the group consisting of 5-deoxygentamicin B,
5-deoxygentamicin $B_1$,
5-deoxygentamicin $C_{1a}$,
5-deoxygentamicin $C_2$,
5-deoxygentamicin $C_{2a}$,
5-deoxygentamicin $X_1$,
5-deoxygentamicin $X_2$,
5-deoxy-Antibiotic 66-40B,
5-deoxy-Antibiotic 66-40D, 5-deoxy-Antibiotic G-418,
5-deoxy-Antibiotic JI-20A,
5-deoxy-Antibiotic JI-20B,
5-deoxyverdamicin,
5-deoxykanamycin B,
5-deoxykanamycin C,
5,3',4'-trideoxykanamycin B,
5-deoxy-Aminoglycoside XK-88-5,
5-deoxytobramycin;

the 1-N-X derivatives thereof wherein X is a substituent selected from the group consisting of —CH$_2$Z and

wherein Z is a member selected from the group consisting of hydrogen, alkyl, alkenyl, cycloalkyl, cycloalkylalkyl, hydroxyalkyl, aminoalkyl, alkylaminoalkyl, aminohydroxyalkyl, alkylaminohydroxyalkyl, phenyl, benzyl, and tolyl, said substituent Z having up to 7 carbon atoms and, when substituted by amino and hydroxy, bearing the substituents on different carbon atoms;

the 2'-N-CH$_2$Z, 6'-N-CH$_2$Z, 1,2'-di-N-CH$_2$Z and the 1,6'-di-N-CH$_2$Z derivatives thereof wherein Z is as hereinabove defined;

5-deoxy-Antibiotic G-52 and the 1-N-X derivatives thereof wherein X is as hereinabove defined;

and the pharmaceutically acceptable acid addition salts thereof;

together with a non-toxic pharmaceutically acceptable carrier.

* * * * *

UNITED STATES PATENT OFFICE
CERTIFICATE OF CORRECTION

Patent No. 4,053,591                    Dated October 11, 1977

Inventor(s) Peter J. L. Daniels et al

It is certified that error appears in the above-identified patent and that said Letters Patent are hereby corrected as shown below:

Column 3, line 13, "and hydrocy" should read ---and hydroxy---.
Column 8, line 64, "sissomicin." should read ---sisomicin.---.
Column 13, line 30, "-N-ethoxycarbponyl-" should read ---N-ethoxycarbonyl---. Column 18, line 15, "-1,3,6',4"-" should read ---1,3,6',3"---; line 26, "-5,2',3',4',2"-" should read ---5,2',3',4',2",4"---.; line 47, "-Benzyol-" should read ---Benzoyl---. Column 19, line 38, ")1.05 molar" should read ---(1.05 molar---. Column 21, line 48, "-2'-O-benzoyl-" should read ---2"-O-benzoyl---. Column 29, line 15, "-1-N-(S-$\delta$-" should read ---1-N-(S-$\gamma$---; line 36, "-amino-60-" should read ---amino-$\alpha$---. Column 33, lines 9-12, "10 mg.     25 mg.     100 mg.
                                        Tab.      Tab.      Tab.

*         *         *
                                       10.5 mg.  26.25 mg.  105.0 mg."

should read  ---10 mg. Tab.   25 mg. Tab.   100 mg. Tab.

10.5* mg.       26.25* mg.    105.0* mg. ---.

*Signed and Sealed this*

Twenty-eighth Day of February 1978

[SEAL]

Attest:

RUTH C. MASON                    LUTRELLE F. PARKER
Attesting Officer      Acting Commissioner of Patents and Trademarks

Notice of Adverse Decision in Interference

In Interference No. 100,087, involving Patent No. 4,053,591, P. L. J. Daniels and S. W. McCombie, 5-DEOXY-4,6-DI-O-(AMINOGLYCOSYL)-1,3-DIAMINOCYCLITOLS, METHODS FOR THEIR MANUFACTURE, METHOD FOR THEIR USE AS ANTIBACTERIAL AGENTS AND COMPOSITIONS USEFUL THEREFOR, final judgment adverse to the patentees was rendered May 24, 1982, as to claims 1, 2, 4, 5, 14 and 15.

[*Official Gazette November 9, 1982.*]